(12) United States Patent
Bishop

(10) Patent No.: US 11,779,645 B2
(45) Date of Patent: *Oct. 10, 2023

(54) COMPOSITIONS COMPRISING WATER THAT EXHIBITS INCREASED CELL PERMEABILITY AND METHODS OF USE THEREOF

(71) Applicant: Hydrosome Labs LLC, Tampa, FL (US)

(72) Inventor: Patrick Charles Bishop, Hoover, AL (US)

(73) Assignee: HYDROSOME HOLDINGS, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/421,163

(22) Filed: May 23, 2019

(65) Prior Publication Data

US 2019/0358169 A1 Nov. 28, 2019

Related U.S. Application Data

(60) Provisional application No. 62/675,248, filed on May 23, 2018.

(51) Int. Cl.

| | |
|---|---|
| A61K 47/02 | (2006.01) |
| A61K 31/00 | (2006.01) |
| A61K 33/00 | (2006.01) |
| A61K 9/00 | (2006.01) |
| A61K 9/08 | (2006.01) |
| A61K 45/06 | (2006.01) |
| A23L 2/52 | (2006.01) |
| B82Y 40/00 | (2011.01) |
| B82Y 5/00 | (2011.01) |
| B82Y 30/00 | (2011.01) |
| C02F 1/00 | (2023.01) |
| C02F 1/28 | (2023.01) |
| C02F 1/32 | (2023.01) |
| C02F 1/34 | (2023.01) |
| C02F 1/42 | (2023.01) |
| C02F 1/44 | (2023.01) |
| C02F 1/469 | (2023.01) |
| C02F 9/00 | (2023.01) |
| A61K 9/51 | (2006.01) |
| A01N 25/28 | (2006.01) |
| C02F 103/04 | (2006.01) |
| C02F 103/02 | (2006.01) |

(52) U.S. Cl.
CPC .............. *A61K 47/02* (2013.01); *A01N 25/28* (2013.01); *A23L 2/52* (2013.01); *A61K 9/0019* (2013.01); *A61K 9/08* (2013.01); *A61K 9/5115* (2013.01); *A61K 9/5123* (2013.01); *A61K 31/00* (2013.01); *A61K 33/00* (2013.01); *A61K 45/06* (2013.01); *B82Y 40/00* (2013.01); *C02F 1/001* (2013.01); *C02F 1/005* (2013.01); *C02F 1/283* (2013.01); *C02F 1/32* (2013.01); *C02F 1/34* (2013.01); *C02F 1/42* (2013.01); *C02F 1/441* (2013.01); *C02F 1/469* (2013.01); *C02F 9/00* (2013.01); *B82Y 5/00* (2013.01); *B82Y 30/00* (2013.01); *C02F 2103/026* (2013.01); *C02F 2103/04* (2013.01); *C02F 2201/002* (2013.01); *C02F 2209/05* (2013.01); *C02F 2209/06* (2013.01); *C02F 2301/024* (2013.01); *C02F 2301/026* (2013.01); *C02F 2303/26* (2013.01)

(58) Field of Classification Search
None
See application file for complete search history.

(56) References Cited

U.S. PATENT DOCUMENTS

| | | |
|---|---|---|
| 6,521,248 B1 | 2/2003 | Holloway et al. |
| 7,832,920 B2 | 11/2010 | Wood et al. |
| 8,193,251 B2 | 6/2012 | Lo et al. |
| 8,623,212 B2 | 1/2014 | Irvin, Sr. et al. |
| 9,474,991 B2 | 10/2016 | Irvin, Sr. |
| 2005/0031657 A1 | 2/2005 | Gilson et al. |
| 2006/0146644 A1* | 7/2006 | Holloway ............... A61P 3/02 366/165.1 |
| 2007/0186367 A1* | 8/2007 | Field ................. A47L 11/4011 15/320 |
| 2011/0218251 A1* | 9/2011 | Lo .......................... B82Y 5/00 514/769 |
| 2012/0039951 A1 | 2/2012 | Watson et al. |

(Continued)

FOREIGN PATENT DOCUMENTS

WO WO-2018179495 A1 * 10/2018 ............... C02F 1/20

OTHER PUBLICATIONS

Riche et al, ("High-Purity Water and pH", American Laboratory (Jun. 2006)), obtained from the website https://www.americanlaboratory.com/913-Technical-Articles/35755-High-Purity-Water-and-pH/ (Year: 2006).*

(Continued)

*Primary Examiner* — Sin J Lee
(74) *Attorney, Agent, or Firm* — Morgan, Lewis & Bockius LLP; Christopher J. Betti

(57) ABSTRACT

The disclosure provides nanometer sized water clusters comprising or consisting essentially of ultrapure water that encapsulate a solute, wherein the water clusters have a median diameter of between about 2 to about 400 nanometers and uses thereof. Also provided by the disclosure are processes and methods for making nanosized water clusters, including processes and methods for encapsulating hydrated solutes in nanosized water clusters.

1 Claim, 8 Drawing Sheets

Figure 1:
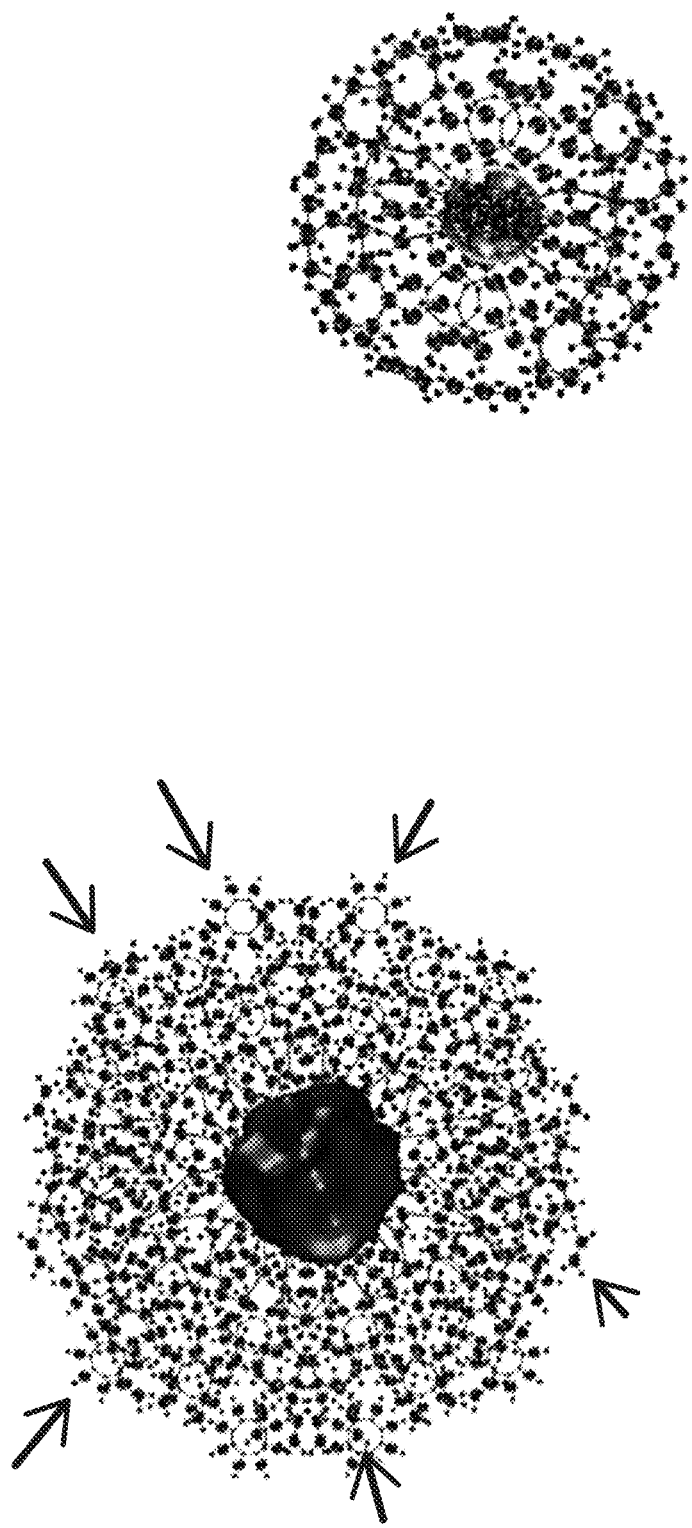

(2 of 8 Drawing Sheet(s) Filed in Color)

(56) References Cited

U.S. PATENT DOCUMENTS

2017/0290854 A1* 10/2017 Matlick ............... A01N 59/00
2020/0121715 A1    4/2020 Bishop et al.

OTHER PUBLICATIONS

"4 Signs You Are Overwatering Your Plants" (Mar. 2017), internet article obtained from the website https://www.brightview.com/resources/article/four-signs-you-are-overwatering-your-plants (Year: 2017).*

"6 Signs You Are Over Fertilizing Your Plants" (Jul. 2017), internet article obtained from the website https://jainsusa.com/blog/6-signs-you-are-over-fertilizing-your-plants/ (Year: 2017).*

Riche et al ("High-Purity Water and pH" an internet article (posted on Jun. 1, 2006) obtained at the website https://www.americanlaboratory.com/913-Technical-Articles/35755-High-Purity-Water-and-pH/#:~:text=The%20resistivity%20of%20ultrapure%20water,and%20the%20pH%20is%206.998.) (Year: 2006).*

Chow et al ("The role of fertilizers in pest control", Nursery Management, Mar. 2010—internet article obtained at the website: https://www.nurserymag.com/article/nmpro-0310-fertilizers-pest-control-roses/#:~:text=The%20compounds%20found%20within%20fertilizers,to%20rapidly%20grow%20and%20multiply) (Year: 2010).*

Third Declaration of Michael Raymond Cary Regarding Public Use and Public Availability of Inventions Claimed in U.S. Appl. No. 16/421,163, dated Jun. 7, 2021, 40 pages.

Declaration of Michael Raymond Cary Regarding Public Use and Public Availability of Inventions Claimed in U.S. Appl. No. 16/421,163, dated Oct. 15, 2020.

Krishan, A., "Rapid flow cytofluorometric analysis of mammalian cell cycle by propidium iodide staining," J Cell Biol., vol. 66, No. (1), (1975), pp. 188-193.

Keutsch, F., Saykally R., "Water clusters: untangling the mysteries of the liquid, one molecule at a time," Proc Natl Acad Sci U S A., vol. 98, No. (19), Sep. 11, 2001 (Sep. 11, 2001), pp. 10533-10540.

Eaves, J.D. et al., "Hydrogen bonds in liquid water are broken only fleetingly," Proc Natl Acad Sci U S A., vol. 102, No. (37), Sep. 13, 2005 (Sep. 13, 2005), pp. 13019-13022.

Plumridge, T.H., Waigh, R.D., "Water structure theory and some implications for drug design," J Pharm Pharmacol., vol. 54, No. (9), (2002), pp. 1155-1179.

Smith, Jared D. et al., "Unified description of temperature-dependent hydrogen-bond rearrangements in liquid water," Proceedings of the National Academy of Sciences of the United States of America, vol. 102, No. (40), Oct. 4, 2005 (Oct. 4, 2005), pp. 14171-14174.

Chaplin, M., "Water's hydrogen bond strength," Cornell University Library, Jun. 10, 2007 (Jun. 10, 2007), pp. 1-20.

Peternelj, A., "Charge and size of particles in surface waters," Master's thesis, Lund University, Jan. 2009 (2009), 91 pages.

Shu, L. et al., "Directly observe sodium chloride aggregates waltzing through dilute solutions," Solutions to Environ. Challenges Through Innovation in Research, (2013), pp. 213-223.

Shirreffs, S., Sawka, M., "Fluid and electrolyte needs for training, competition, and recovery," J Sports Sci. vol. 29, No. (S1), Dec. 9, 2011 (Dec. 9, 2011), pp. S39-S46.

Tomaszewska, E. et al., "Detection limits of DLS and UV-Vis spectroscopy in characterization of polydisperse nanoparticles colloids," J. of Nanomaterials, vol. 2013, Jul. 17, 2013 (Jul. 17, 2013), pp. 1-10.

Gravelle, S. et al., "Optimizing water permeability through the hourglass shape of aquaporins," Proceedings of the National Academy of Sciences of the United States of America, vol. 110, No. (41), Oct. 8, 2013 (Oct. 8, 2013), pp. 16367-16372.

Stoyanov, Evgenii S. et al., "The structure of the hydrogen ion (H(aq)+) in water," Journal of the American Chemical Society, vol. 132, No. (5), Feb. 10, 2010 (Feb. 10, 2010), 7 pages.

Del Giudice, E. et al., "The origin and the special role of coherent water in living systems," Fields of the Cell, (2015), pp. 95-111.

Nestle Pure Life, Bottled Water Quality Report, REV Dec. 31, 2015, 14 pages, Nestle Waters North America Inc., 900 Long Ridge Rd., Stamford CT 06902.

Dehydration, from Wikipedia the free encyclopedia on the Internet, last edited Jan. 30, 2018, 5 pages.

Aquaporin, from Wikipedia the free encyclopedia on the Internet, last edited Jan. 31, 2018, 12 pages.

Purified water, from Wikipedia the free encyclopedia on the Internet, last edited Feb. 8, 2018, 8 pages.

Water cluster, from Wikipedia the free encyclopedia and Wikivisually on the Internet, last edited in 2018, 5 pages.

Second Declaration of Michael Raymond Cary Regarding Public Use and Public Availability of Inventions Claimed in U.S. Appl. No. 16/421,163, dated Apr. 16, 2021, 36 pages.

* cited by examiner

COMPOSITIONS COMPRISING WATER THAT EXHIBITS INCREASED CELL PERMEABILITY AND METHODS OF USE THEREOF

CROSS REFERENCE TO RELATED APPLICATIONS

The present application claims priority to U.S. Provisional Patent Application Ser. No. 62/675,248, filed on May 23, 2018, which is incorporated herein by reference in its entirety.

FIELD

The present disclosure generally relates to compositions that comprise ultrapure water and one or more solutes, wherein the ultrapure water forms a water cluster that encapsulates a solute.

BACKGROUND

A large portion of water molecules present in a solution exist in water clusters formed by hydrogen bonds of varying strengths and varying duration. These water clusters typically exist in large, steady state structures comprising approximately 2000 to 5000 water molecules. Additionally, the relatively unstable nature of a water cluster typically causes it to exclude solutes, incompletely encapsulate solutes, or be present in a disordered state relative to solutes.

The structure of water molecules in a solution is known to have implications for drug design and delivery. (Plumridge & Waigh, 2002, Water structure theory and some implications for drug design, J. Pharmacy & Pharmacology Vol. 54, 1155-1179.) Indeed, the structure of water molecules can impede the interaction of a dissolved solute with its receptor or its transport across a cell membrane. Further, the structure of water molecules can influence the solubility and stability of a dissolved solute. As such, there exists a need for compositions that comprise water molecules and a solute that have improved bioavailability, solubility, and/or stability.

SUMMARY

The present disclosure provides compositions or solutions that include water clusters (e.g., nanosized water clusters) that comprise or consist essentially of ultrapure water. Optionally, the water clusters may encapsulate a solute. In some embodiments, the water clusters are nanosized (e.g., have a median size (diameter) of between about 2 to about 400 nanometers).

In some embodiments, the water clusters comprise about 25, about 30, about 35, about 40, about 45, about 50, about 75, about 100, about 125, about 150, about 175, about 200, about 225, about 250, about 275, about 300, about 325, about 350, about 375, about 400, about 425, about 450, about 475, or about 500 water molecules.

In some embodiments of each or any of the above- or below-mentioned embodiments, the water clusters have a median size (diameter) of between about 2 to about 400 nanometers. In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 15 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers.

In an embodiment of each or any of the above- or below-mentioned embodiments, the solute encapsulated within a water cluster has improved bioavailability relative to an unencapsulated solute. In further embodiments, the solute encapsulated within a water cluster has improved stability relative to an unencapsulated solute. In still further embodiments, the solute encapsulated within a water cluster has improved solubility relative to an unencapsulated solute.

In an embodiment of each or any of the above- or below-mentioned embodiments, the solute encapsulated in a water cluster comprises a small molecule drug, a protein, a peptide, or a combination thereof. In some embodiments, the solute encapsulated in a water cluster comprises a cellular detoxification agent, a hydration agent, an anti-inflammatory agent, a neuroprotective agent, a neuromodulatory agent, or an anti-tumorigenic agent. In still other embodiments, the solute encapsulated in a water cluster improves ATP production.

In an embodiment of each or any of the above- or below-mentioned embodiments, the solute comprises an electrolyte (e.g., an electrolyte solution). In an exemplary embodiment, the electrolyte solution is a component of a hydration, sports or energy drink. In still further embodiments, the electrolyte solution comprises a sugar, vitamin c, a magnesium cation, a chloride anion, a sodium cation, a potassium cation, a sulfate anion, a boron cation, or a sodium substitute.

In an embodiment of each or any of the above- or below-mentioned embodiments, the solute encapsulated in a water cluster comprises a fertilizer.

In an embodiment of each or any of the above- or below-mentioned embodiments, the solute encapsulated in a water cluster comprises an ion of an ionizable salt. In certain embodiments, the ion is selected from an aluminum ion, an ammonium ion, an antimony ion, an arsenic ion, a barium ion, a beryllium ion, a bismuth ion, a boron ion, a bromide ion, a cadmium ion, a calcium ion, a cerium ion, a cesium cation, a chloride ion, a chromium ion, a cobalt ion, a copper ion, a dysprosium ion, an erbium ion, an europium ion, a fluoride ion, a gadolinium ion, a gallium ion, a germanium ion, a gold ion, a hafnium ion, a holmium ion, an indium ion, an iodine ion, an iridium ion, an iron ion, a lanthanum ion, a lead ion, a lithium ion, a lutetium ion, a magnesium ion, a manganese ion, a mercury ion, a molybdenum ion, a neodymium ion, a nickel ion, a niobium ion, an osmium ion, a palladium ion, a phosphorus ion, a platinum ion, a potassium ion, a praseodymium ion, a rhenium ion, a rhodium ion, a rubidium ion, a ruthenium ion, a samarium ion, a scandium ion, a selenium ion, a silicon ion, a silver ion, a sodium ion, a strontium ion, a sulfate ion, a tantalum ion, a tellurium ion, a terbium ion, a thallium ion, a thorium ion, a thulium ion, a tin ion, a titanium ion, a tungsten ion, a vanadium ion, an ytterbium ion, an yttrium ion, a zinc ion, and a zirconium ion.

In an embodiment of each or any of the above- or below-mentioned embodiments, the composition or solution is stable for at least about 2.5 years.

In some embodiments of each or any of the above- or below-mentioned embodiments, the water clusters comprise or consist essentially of ultrapure water having a high negative oxidative reduction potential. In further embodiments, the oxidative reduction potential of the ultrapure water is about 140 to about 160 mV (e.g., about 140 mV, about 145 mV, about 150 mV, about 155 mV, or about 160 mV). In still further embodiments, the pH of the ultrapure water is between about 4 to about 6 (e.g., about 4, about 5, or about 6).

In some embodiments of each or any of the above- or below-mentioned embodiments, the composition or solution is used to deliver a solute to the interior of a cell (e.g., a plant or an animal cell).

In some embodiments of each or any of the above- or below-mentioned embodiments, the composition or solution is used to deliver a pharmaceutical agent to a cell. In some embodiments, the composition or solution is used to deliver a solute to a subject in need thereof. In certain embodiments, the composition or solution is used to deliver a cellular detoxification agent, a hydration agent, an anti-inflammatory agent, a neuroprotective agent, a neuromodulatory agent, and/or an anti-tumorigenic agent. In some embodiments, the composition or solution is used to deliver a solute intravenously.

In some embodiments of each or any of the above- or below-mentioned embodiments, the solute comprises potassium chloride, vitamin B6, ferric chloride, magnesium sulfate, sodium chloride, ionic trace minerals, kelp, taurine, alfalfa, or sodium borate. In other embodiments, the solute comprises capasaicin, resveratrol, quercetin, vitamin d3, or *Panax ginseng*. In still other embodiments, the solute comprises synapta, magnesium chloride, concentrated trace minerals, or sodium benzoate.

In some embodiments of each or any of the above- or below-mentioned embodiments, the composition or solution is used for an agricultural application. In some embodiments, the composition or solution is used for fertilizer delivery, soil or plant hydration, heat tolerance, or seed germination. In further embodiments, the composition or solution is used in livestock management.

The present disclosure also provides a composition or a solution that includes water clusters that comprise or consist essentially of ultrapure water, wherein the water clusters have a median diameter of between about 2 to about 400 nanometers, and wherein the water clusters optionally have improved bioavailability relative to a composition or a solution that does not include water clusters that comprise or consist essentially of ultrapure water. In some embodiments, the water clusters have a median of about 150 to about 300 water molecules per water cluster. In other embodiments, the water clusters have a median of about 25, about 30, about 35, about 40, about 45, about 50, about 75, about 100, about 125, about 150, about 175, about 200, about 225, about 250, about 275, about 300, about 325, about 350, about 375, about 400, about 425, about 450, about 475, or about 500 water molecules per water cluster.

The present disclosure also provides methods for improving the bioavailability of a solute. In certain embodiments, the methods comprise dissolving the solute in ultrapure water and encapsulating the solute in a water cluster, wherein the water cluster is between about 2 to about 400 nanometers in median diameter. In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 20 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers. In some embodiments, the solute is a small molecule drug, a protein, a peptide, a detoxification agent, a hydration agent, an anti-inflammatory agent, a neuroprotective agent, a neuromodulatory agent, or an anti-tumorigenic agent. In some embodiments, the solute is an electrolyte including, for example, an electrolyte contained in a hydration, sports or energy drink.

The present disclosure also provides methods for dissolving a solute in ultrapure water comprising mixing the solute with ultrapure water and encapsulating the solute in water clusters with a median diameter of between about 2 to about 400 nanometers. In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 20 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers.

In some embodiments of each or any of the above- or below-mentioned embodiments, the disclosure provides a pharmaceutical composition that includes water clusters comprising or consisting essentially of ultrapure water, wherein the water clusters have a median water cluster diameter of between about 2 to about 400 nanometers, and wherein the water clusters encapsulate a solute. In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 20 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers. In certain embodiments, the solute comprises a small molecule drug, a protein, or a peptide. In certain embodiments, the solute comprises a hydration agent, an anti-inflammatory agent, a neuroprotective agent, a neuromodulatory agent, or an anti-tumorigenic agent. In certain embodiments, the solute comprises Vectcytotratin.

The present disclosure also provides a hydration, sports, or energy drink that includes water clusters that comprise or consist essentially of ultrapure water, wherein the water clusters have a median water cluster diameter of between about 2 to about 400 nanometers, and wherein the water clusters encapsulate a solute (e.g., an electrolyte). In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 20 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers. In certain embodiments, the solute comprises aluminum, boron, calcium, chloride, copper, fluoride, iodine, iron, magnesium, phosphorus, potassium, rubidium, silicon, sodium sulfate, titanium, zinc, and/or zirconium. In certain embodiments, the solute comprises potassium, vitamin b6, iron, magnesium, chloride, sodium, ionic trace minerals, sulfate, kelp, taurine, alfalfa, and/or boron.

The present disclosure also provides a fertilizer that includes water clusters comprising or consisting essentially of ultrapure water, wherein the water clusters have a median water cluster diameter of between about 2 to about 400 nanometers, and wherein the water clusters encapsulate a solute. In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 20 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers. In certain embodiments, the solute comprises nitrogen, phosphorous, potassium, calcium, magnesium, ammonium, sulfur, copper, iron, manganese, molybdenum, zinc, boron, silicon, cobalt, vanadium and/or urea.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 illustrates a large water cluster comprising approximately 2,000 water molecules (left) and a water cluster provided by the disclosure (right) comprising approximately 200 water molecules.

FIG. 2 is a flow chart depicting a process for producing water clusters according to embodiments of the disclosure.

FIG. 3 shows the size distribution of conventional water structures (e.g., water structures that do not include water clusters comprising or consisting essentially of ultrapure water) (top) and water structures of the present disclosure that comprise or consist essentially of ultrapure water.

FIG. 4 shows results of a human cell absorption study demonstrating that propidium iodide (PI) encapsulated by the water clusters of the present disclosure is able to access the interior of a cell nuclei at 10 and 30 minutes ("NanoPI," top and bottom right, respectively), whereas propodium iodiode in control water (e.g., water that does not include water clusters comprising or consisting essentially of ultrapure water) is not able to enter the cells ("Macro PI Control" at left).

FIG. 5 shows the results of a sod farm study with sod watered with 40 gallons of control water with dissolved fertilizer prepared conventionally (left) and 20 gallons of water prepared with fertilizer encapsulated in water clusters according to embodiments of the disclosure (right).

FIG. 6 shows the results of a 3-day alfalfa sprouting study using control water (left), macromineral supplement (center), and a macromineral supplement encapsulated in water clusters (labeled "hydrosome") according to embodiments of the disclosure.

FIG. 7 shows the results of a 15-day pea sprouting study using control water (right), water with dissolved fertilizer prepared conventionally (center), and water prepared with fertilizer encapsulated in water clusters according to embodiments of the disclosure (left) ("hydrosome delivery").

FIG. 8 shows the results of a safflower growth study in drought conditions, including root structures. Fields were watered with the same amount of fertilizer. Plants were watered with dissolved fertilizer prepared conventionally (left), and water prepared with fertilizer encapsulated in water clusters according to embodiments of the disclosure (right).

DETAILED DESCRIPTION

The present disclosure provides compositions and solutions that include water clusters comprising or consisting essentially of ultrapure water and a solute (sometimes referred to herein as hydrosomes) and methods of using the same. The inventors have surprisingly found that ultrapure water, unlike water having one or more impurities, can be disassociated into smaller water clusters (e.g., water clusters comprising about 2,000 to about 5,000 water molecules can be stably reduced to a nanosized water cluster comprising about 100 to about 500 water molecules). The water clusters having ultrapure water can advantageously be used to encapsulate a solute (e.g., an organic chemical, an inorganic chemical, a protein, a peptide, a sugar, an oligosaccharide, a polysaccharide, a synthetic polymer, a fat, a wax, an oil, a colloid, a fatty acid, a DNA nucleotide, a polynucleotide, an RNA polynucleotide, a pharmaceutical drug, a fertilizer, or an electrolyte) and optionally used to deliver the solute across a cell membrane to exert its effect. As such, the disclosed compositions and solutions provide surprising and unexpected advantages in various applications, including medical and agricultural applications, based, for example, on the improved bioavailability, solubility, and/or stability of water clusters comprising or consisting essentially of ultrapure water, and solutes encapsulated in water clusters comprising or consisting essentially of ultrapure water.

Also provided by the present disclosure are methods for making nanosized water clusters (e.g., from ultrapure water), including methods for encapsulating a solute in a water cluster comprising or consisting essentially of ultrapure water.

The water clusters comprising or consisting essentially of ultrapure water may be used to encapsulate nutrients, foods, pharmaceuticals, biologic drugs, biotechnology products, inorganic or organic chemicals. Additionally, in some embodiments, the water clusters comprising or consisting essentially of ultrapure water may be used to encapsulate a solute for human and/or animal nutrition, or agriculture production. In still further embodiments, the water clusters comprising or consisting essentially of ultrapure water may be used to encapsulate a solute in a hydration, sports, or energy drink. In other embodiments, the water clusters comprising or consisting essentially of ultrapure water may be used as a means for creating oral drug formulations with improved drug pharmacokinetics, higher drug bioavailability, increased drug safety and/or higher selective potency. Further, in other embodiments, the water clusters comprising or consisting essentially of ultrapure water may be used to encapsulate a drug or a biotechnology product.

In some embodiments, the disclosure provides compositions and solutions that include water clusters comprising or consisting essentially of ultrapure water and a solute, wherein the ultrapure water forms a water cluster that encapsulates a solute.

In certain embodiments, the water clusters in the composition have a median size of between about 2 to about 400 nanometers. In another embodiment, the water clusters have a median size of between about 2 to about 10 nanometers (e.g., about 2 nanometers, about 3 nanometers, about 4 nanometers, about 5 nanometers, about 6 nanometers, about 7 nanometers, about 8 nanometers, about 9 nanometers, or about 10 nanometers). In other embodiments, the water clusters have a median size of between about 10 to about 20 nanometers or about 15 to about 20 nanometers, or about 20 to about 25 nanometers. In other embodiments, the water clusters have a median size of between about 10 to about 50 nanometers, about 20 to about 50 nanometers, about 30 to about 50 nanometers, or about 40 to about 50 nanometers. In still other embodiments, the water clusters have a median size of between about 50 to about 100 nanometers. In yet further embodiments, the water clusters have a median size of between about 100 to about 200 nanometers, about 150 to about 200 nanometers, about 200 to about 300 nanometers, about 250 to about 300 nanometers, or about 300 to about 400 nanometers.

The present disclosure also provides compositions and solutions wherein 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the composition or solution includes water clusters comprising or consisting essentially of ultrapure water and a solute, wherein the ultrapure water forms water clusters that encapsulate the solute.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the water clusters in the composition or solution encapsulate the solute.

Where the term "comprising" is used in the present description and the claims, it does not exclude other elements or steps. For the purposes of the present invention, the term "consisting of" is considered to be a preferred embodiment of the term "comprising".

Specific embodiments disclosed herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

In cases where numerical values are indicated in the context of the present disclosure, the skilled person will understand that the technical effect of the feature in question is ensured within an interval of accuracy, which typically encompasses a deviation of the numerical value given of ±10%, and preferably of ±5%. At the very least, and not as an attempt to limit the application of the doctrine of equivalents to the scope of the claims, each numerical parameter should at least be construed in light of the number of reported significant digits and by applying ordinary rounding techniques.

Unless otherwise indicated, all numbers expressing quantities of ingredients, properties such as molecular weight and median size, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments of this disclosure are described herein, including the best mode known to the inventor for carrying out the disclosure. Of course, variations on these described embodiments will become apparent to those of ordinary skill in the art upon reading the foregoing description. The inventor expects skilled artisans to employ such variations as appropriate, and the inventor intends for the disclosure to be practiced other than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

Further definitions of terms will be given in the following in the context of which the terms are used. The following terms or definitions are provided solely to aid in the understanding of the invention. These definitions should not be construed to have a scope less than understood by a person of ordinary skill in the art.

As used herein, a "water cluster" refers to an assembly of water molecules bonded with or otherwise associated with one another by electrostatic forces, such as hydrogen bonding, ionic bonding, van der Waals forces, or the like. In some cases according to the disclosure, a water cluster further comprises a solute associated with the water molecules and encapsulated within the water cluster. The water clusters of the present disclosure preferably comprise or consist essentially of ultrapure water.

As used herein, a "solute" means a substance or particle that is fully or partially dissolved in ultrapure water. In embodiments, a solute of the disclosure is encapsulated within a water cluster of the disclosure. A solute according to the disclosure comprises, without limitation, a polar or non-polar substance, a liquid, a solid, a lipid, a protein, a peptide, a nucleic acid, an organic compound, an inorganic compound, or any combination thereof.

As used herein, a "hydration agent" means, a substance that promotes the hydration of, without exclusion, a cell, a plant, a human or non-human animal, or a soil sample.

As used herein, an "encapsulated solute" means a solute substantially enclosed within a water cluster according to the disclosure.

As used herein, an "unencapsulated solute" is a solute that is not contained within a water cluster, or is not contained within a water cluster with a median diameter between about 2 to about 400 nanometers, or is not contained within a water cluster produced by the methods, processes, and/or apparatus of the disclosure.

As used herein, "ultrapure water" means water prepared according to one or more of the described embodiments of the disclosure. In particular, ultrapure water refers to water prepared by methods and processes disclosed herein, or water characterized as being completely free of (e.g., does not contain any detectable amount), or substantially free of (e.g., 70%, 80%, 90%, or 95% free of), one or more impurities or contaminants.

As used herein, "bioavailability" refers to the physiological availability of a given amount of a solute as distinct from its chemical potency. For example, bioavailability refers to the proportion of an administered solute that is absorbed into the bloodstream of a mammal or is absorbed into the tissues of a plant. Bioavailability also refers to the ability of a water cluster, solute, particle, encapsulated solute, or combination thereof, to access a biological target, e.g., by crossing a biological membrane or by interacting with a biological receptor or other binding partner.

The disclosure provides compositions and solutions comprising water clusters that comprise or consist essentially of ultrapure water and optionally a solute encapsulate by the water clusters. The water cluster may have a median water cluster size of between about 2 to about 400 nanometers or a median of about 10 to about 500 water molecules per water cluster.

In some embodiments, the ultrapure water of the disclosure comprises water substantially free of or completely free of contaminants (e.g., an impurity). As used herein, a contaminant is a foreign substance not intentionally added to the ultrapure water produced according to the disclosure. Thus, ultrapure water substantially free of contaminants contains undetectable levels/amounts of, for example, the following contaminants: (a) pathogenic bacteria (e.g., fecal coliform), viruses (e.g., hepatitis viruses, hemorrhagic viruses, retroviruses such as AIDS virus), fungi, mycoplasm, protozoa, prokaryotes, protists, parasites, microorganisms causing infectious diseases, and their spores, eggs, DNA, RNA, or related reproductive constituents, prions, (b) toxic biochemicals including toxic proteins, lipids, carbohydrates, toxic nucleic acids, known carcinogens, and chemotherapy drugs; (c) toxic inorganic chemicals (soluble and insoluble in water and including toxic heavy metals) and their particles; (d) toxic organic chemicals (soluble and insoluble in water and including pesticides) and their particles; (e) non-water organic liquids (miscible and immiscible); (f) radioactive minerals, or (g) toxic gases including ammonia, arsenic pentafluoride, arsine, bis(trifluoromethyl)peroxide, boron tribromide, boron trichloride, boron trifluoride, bromine, bromine chloride, boromethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde, germane, hexylethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perfluroisobuytlene, phosgene, phosphine, phosphorus pentafluoride, selenium hexafluoride, silicon hexafluoride, silicon tetrachloride, stilbene, disulfur decafluoride, sulfur tetrafluoride, tellurium hexafluoride, tetraethyl pyrophosphate, tetraethyl dithiopyrophosphate, trifluoroacetyl chloride, tungsten hexafluoride, and radon.

Figure 2:
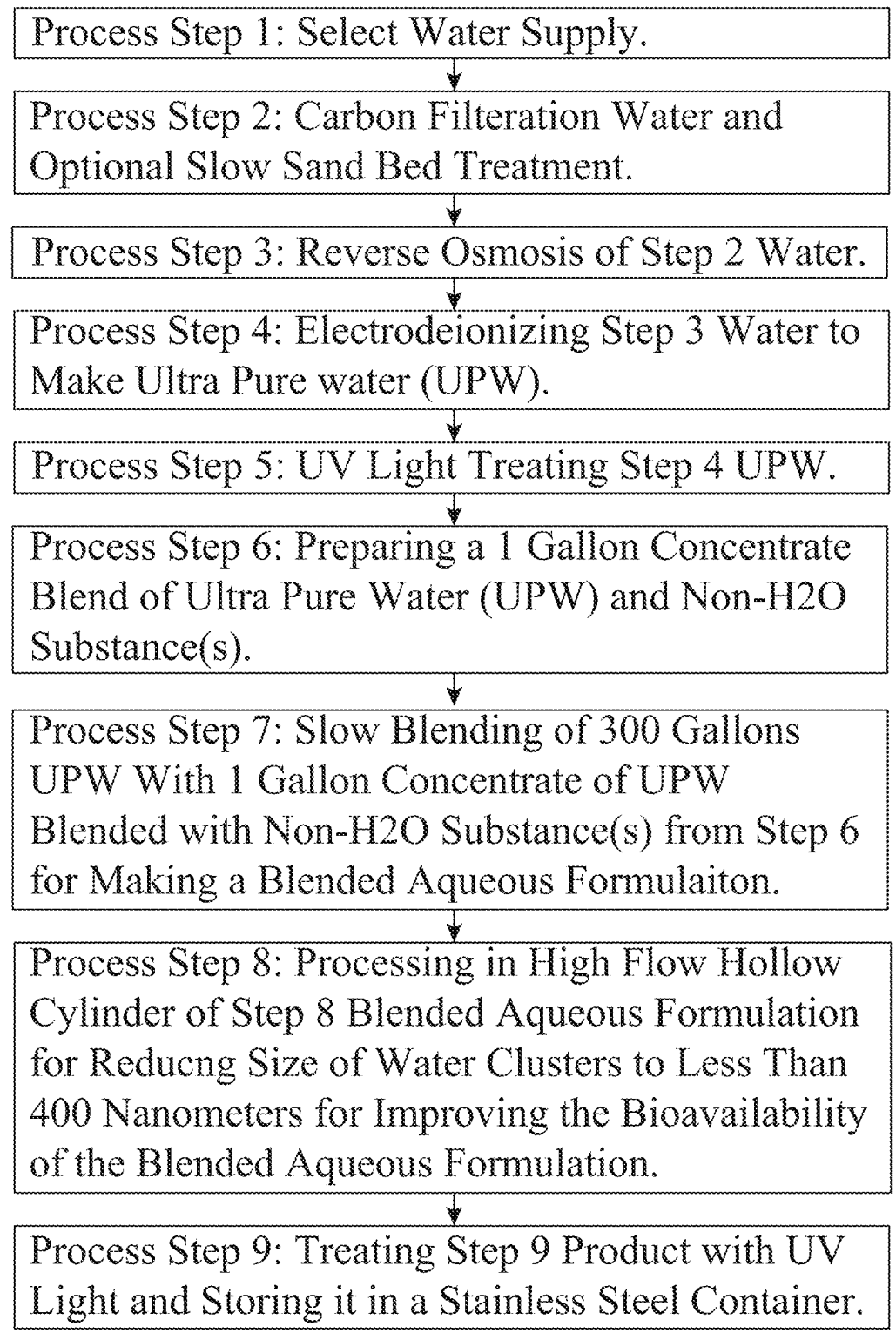

The ultrapure water of the disclosure may be prepared by processes known in the art and used as a starting material for generating the compositions and solutions comprising water clusters as disclosed herein. The ultrapure water of the disclosure may be prepared by carbon filtration, by slow sand filtration, by reverse osmosis, by electro-deionization treatment, by ultraviolet light exposure, or by a combination comprising two or more of the processes described herein. For example, the ultrapure water of the disclosure may be prepared by a sequential process comprising each of carbon filtration, slow sand filtration, reverse osmosis, electro-deionization treatment, and ultraviolet light exposure. For example, FIG. 2 of the disclosure presents a flow chart of steps including water purification steps according to one embodiment. Alternatively, the ultrapure water may be prepared according to one or more of the processes desribed herein in combination with other methods of water purification known in the art but not expressly recited herein.

The ultrapure water may be prepared by a process comprising the steps of: filtering a volume of water with a carbon filter to produce an amount of water with a low chlorine content; removing ions in the carbon filtered water by a reverse osmosis process to produce a supply of a deionized water; electro-deionizing the supply of the deionized water from the reverse osmosis process to make an ultrapure water supply; testing the resistivity of the ultrapure water to determine if the resistivity of the ultrapure water is between about 17 meg-ohm cm to about 18.2 meg-ohm cm; repeating a process step for preparing the ultrapure water and retesting the resistivity of the ultrapure water until the ultrapure water has a measured resistivity of between about 17 meg-ohm cm to about 18.2 meg-ohm cm; irradiating the supply of the ultrapure water having a measured resistivity of between about 17 meg-ohm cm to about 18.2 meg-ohm cm with ultraviolet light to make a sterilized ultrapure water supply; and storing the sterilized ultrapure water in a stainless steel container until sterilized ultrapure water is needed to be added in the process to make an aqueous composition comprising an aqueous medium with reduced size water clusters containing a solute to improve bioavailability of the aqueous composition.

The ultrapure water is purified of contaminants including, for example, organic and inorganic compounds; dissolved and particulate matter; volatile and non-volatile matter; reactive and inert matter; hydrophilic and hydrophobic matter; and dissolved gases. Ultrapure water and commonly used term deionized (DI) water are not the same. An ultrapure water system may include three stages: a pretreatment stage to produce purified water, a primary stage to further purify the water, and a polishing stage. The most widely used requirements for ultrapure water quality are documented by ASTM D5127 "Standard Guide for Ultra-Pure Water Used in the Electronics and Semiconductor Industries" and SEMI F63 "Guide for ultrapure water used in semiconductor processing."

The polishing stage may include continuously treating and recirculating the purified water in order to maintain stable high purity quality of supplied water. Traditionally the resistivity of water serves as an indication of the level of purity of ultrapure water. Deionized (DI) water may have a purity of at least one million ohms-centimeter or one meg-ohm cm. In a preferred embodiment, the ultrapure water quality is at the theoretical maximum of water resistivity (18.18 meg-ohm cm at 25° C.).

The ultrapure water of the disclosure may have a high oxidative reduction potential including, for example, about 140 to about 160 mV. Further, the pH of the ultrapure water may be between about 3 to about 7, preferably about 4 to about 6 and the resistivity of the ultrapure water may be between about 17 to about 18.2 meg-ohm cm.

In some embodiments, the compositions and solutions include water clusters comprising or consisting essentially of ultrapure water, wherein the water clusters encapsulate a solute, and wherein the ultrapure water has a high negative oxidative reduction potential. In further embodiments, the oxidative reduction potential of the ultrapure water is about 80 mV to about 100 mV, about 100 mV to about 120 mV, about 120 mV to about 140 mV, or about 140 mV to about 160 mV. In still further embodiments, the pH of the ultrapure water is between about 4 to about 5, about 5 to about 6, or about 6 to about 7.

A solute encapsulated in a water cluster comprising or consisting essentially of ultrapure water may be a small molecule drug, a protein, a peptide, or a combination thereof. In some embodiments, the solute comprises a cellular detoxification agent, a hydration agent, an anti-inflammatory agent, a neuroprotective agent, a neuromodulatory agent, or an anti-tumorigenic agent. In still other embodiments, the solute improves ATP production.

Solutes suitable for use in embodiments of the disclosure may have an approximately round geometry, a flat plate geometry, a cube geometry, a rod-like geometry, a hollow geometry, and/or a semi-hollow geometry. In some embodiments, a solute encapsulated in a water cluster comprising or consisting essentially of ultrapure water may comprise a primary solute, a mixture of a first solute and a second solute, or a plurality of solutes. The solutes may have one or more additional associated solutes, such as a surface coating, as a subsurface coating, or in a complex with other solutes. The solutes may comprise a liquid, a solid, or be a colloidal system with a colloid and a dispersing agent.

In some embodiments, the solute comprises an organic chemical, an inorganic chemical, a fat, a peptide, a sugar, a synthetic polymer including polyethylene, nylon, polypropylene, a wax, an oil, a colloid, an oligosaccharide, a polysaccharide, a protein, a fatty acid, a DNA nucleotide, a polynucleotide, an RNA polynucleotide, a pharmaceutical drug, a surfactant, a hydrogel, a hydrophilic substance catalyst, a free radical scavenger, an ion chelator, avidin, steptavidin, a paramagnetic substance, a magnetic field sensitive substance, a radioactive substance, a radiocontrast agent, an ultrasound contrast agent, a cerium oxide, an oderant, a perfume, a pheromone, a hormone, a cytokine, an interleukin, blebbistatin, a blebbistatin derivative, Vectcytotratin, Keytruda®, an antibody, a biological cell organelle, an intact biological, a fluorescent compound, a polymerase, a P450 enzyme, a PCR enzyme, a catalyst, or any combination thereof.

In some embodiments, the solute comprises a pharmaceutical drug selected from: an opiate, e.g. morphine, buprenorphine, oxymorphone, hydromorphone, codeine, hydrocodone, oxycodone, tramadol, and the like; ibogain, or related psychoactives; or a phosphodiesterase 5 inhibitor, e.g. Sildenafil (Viagra), Tadalafil (Cialis), or Vardenafil (Levitra).

In certain embodiments, a solute encapsulated in a water cluster comprising or consisting essentially of ultrapure water is an ion of an ionizable salt. In certain embodiments, the ion is an aluminum ion, ammonium ion, antimony ion, arsenic ion, barium ion, beryllium ion, bismuth ion, boron ion, bromide ion, cadmium ion, calcium ion, cerium ion, cesium cation, chloride ion, chromium ion, cobalt ion, copper ion, dysprosium ion, erbium ion, europium ion, fluoride ion, gadolinium ion, gallium ion, germanium ion, gold ion, hafnium ion, holmium ion, indium ion, iodine ion, iridium ion, iron ion, lanthanum ion, lead ion, lithium ion, lutetium ion, magnesium ion, manganese ion, mercury ion, molybdenum ion, neodymium ion, nickel ion, niobium ion, osmium ion, palladium ion, phosphorus ion, platinum ion, potassium ion, praseodymium ion, rhenium ion, rhodium ion, rubidium ion, ruthenium ion, samarium ion, scandium ion, selenium ion, silicon ion, silver ion, sodium ion, strontium ion, sulfate ion, tantalum ion, tellurium ion, terbium ion, thallium ion, thorium ion, thulium ion, tin ion, titanium ion, tungsten ion, vanadium ion, ytterbium ion, yttrium ion, zinc ion, or zirconium ion.

The water clusters comprise or consist essentially of ultrapure water and have a median diameter of between about 2 to about 400 nanometers or comprise about 10 to about 500 molecules of water per cluster (e.g., per hydrosome). In certain embodiments, the water clusters have a median diameter of about 1 nanometers, about 2 nanometers, about 3 nanometers, about 4 nanometers, about 5 nanometers, about 6 nanometers, about 7 nanometers, about 8 nanometers, about 9 nanometers, about 10 nanometers, about 11 nanometers, about 12 nanometers, about 13 nanometers, about 14 nanometers, about 15 nanometers, about 16 nanometers, about 17 nanometers, about 18 nanometers, about 19 nanometers, or about 20 nanometers. In other embodiments, the water clusters according to the disclosure comprise a median diameter of about 20 nanometers, about 22 nanometers, about 24 nanometers, about 26 nanometers, about 28 nanometers, or about 30 nanometers. In still other embodiments, the water clusters according to the disclosure comprise a median diameter of about 35 nanometers, about 40 nanometers, about 45 nanometers, about 50 nanometers, about 60 nanometers, about 70 nanometers, about 80 nanometers, about 90 nanometers, or about 100 nanometers.

In some embodiments, the water cluster comprises about 20, about 25, about 30, about 35, about 40, about 45, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 water molecules. In other embodiments, the water cluster comprises between about 50 and about 100 water molecules, about 100 to about 150 water molecules, about 150 to about 200 water molecules, about 200 to about 250 water molecules, about 250 to about 300 water molecules, about 300 to about 350 water molecules, about 350 to about 400 water molecules, about 400 to about 450 water molecules, or about 450 to about 500 water molecules.

In some embodiments, the water cluster fully encapsulates a solute or substantially encapsulates a solute (e.g., encapsulates about 50%, 55%, 60%, 65%, 70%, 80%, 85%, 90%, 95% or more of the solute).

Those skilled in the art will recognize different ways of measuring a diameter of a water cluster of the disclosure. In an exemplary method a diameter of a water cluster is measured using a Malvern Instruments Zetasizer Nano ZSP, which is a high performance system and particularly suitable for the characterization of water clusters, solutes, e.g. proteins and other nanoparticles. Optionally, the particle size measurements for the Zetasizer Nano are automated using a NanoSampler.

In some embodiments, the water cluster and solutes of the disclosure are measured according to the following non-limiting parameters: water cluster diameter, particle and molecule size, translational diffusion, electrophoretic mobility, zeta potential of particles at high and low concentrations, viscosity and viscoelasticity of protein and polymer solutions, concentration, and/or molecular weight (e.g. $k_D$).

In some embodiments, the water clusters comprising or consisting essentially of ultrapure water are stable for an extended storage period including, for example, a period of years. In some embodiments, the water clusters are stable for about 2 years, about 4 years, about 6 years, about 8 years, or about 10 years. In some embodiments, the water clusters are stable for a period in excess of 10 years.

In some embodiments, the water clusters stably encapsulate a solute for a period of years, for example for about 2 years, about 4 years, about 6 years, about 8 years, or about 10 years. In further embodiments, the water clusters stably encapsulate a solute for a period in excess of 10 years.

In some embodiments, the compositions or solutions include water clusters comprising or consisting essentially of ultrapure water, wherein the ultrapure water has a high negative oxidative reduction potential including, for example, an oxidative reduction potential of about 140 to about 160 mV. In still further embodiments, the pH of the ultrapure water is between about 4 to about 6.

In some embodiments, the disclosure provides compositions or solutions for use in delivering a solute to the interior of a cell. In other embodiments, the disclosure provides compositions or solutions for use in delivering a solute to the interior of a plant or an animal cell.

Embodiments of the disclosure include compositions or solutions wherein a solute is encapsulated within a water cluster and has improved bioavailability relative to a composition or a solution where the solute is unencapsulated by a water cluster. In some embodiments, the solute encapsulated within a water cluster has improved bioavailability by virtue of its ability to access the interior of a cell. For example, a water having an impurity or a solute is typically incapable of passing through a cell membrane, but a solute encapsulated within the water clusters of the disclosure are able to cross a cell membrane. In some embodiments, a cell membrane may be a plasma membrane, a nuclear membrane, a cell wall, or any other impermeable barrier defining the boundaries of a cell or an organelle within a cell.

In other embodiments, a solute encapsulated within a water cluster comprising or consisting essentially of ultrapure water has improved bioavailability by virtue of its ability to access an intracellular space. In still other embodiments, the solute encapsulated within a water cluster has improved bioavailability by virtue of its ability to access specific plant or animal tissue types, such as root or leaf tissue in a plant, or skin or internal organ tissues in an animal. In yet other embodiments, a water cluster comprising or consisting essentially of ultrapure water has improved bioavailability relative to a water cluster that does not comprise ultrapure water.

In some embodiments, the water clusters and encapsulated solutes have improved bioavailability relative to naturally occurring water and dissolved solutes. In some embodiments, the water clusters and encapsulated solutes provided herein render an otherwise unavailable solute bioavailable, in which case the disclosure provides improved bioavailability of the solute relative to the unencapsulated solute. In other embodiment, the water clusters comprising or consisting essentially of ultrapure water, wherein the water clusters encapsulate a solute improve bioavailability of the solute by about 10%, about 20%, about 30%, about 40%, about 50%, about 60%, about 70%, about 80%, or about 90% relative to the unencapsulated solute. In further embodiments, the water clusters comprising or consisting essentially of ultrapure water and encapsulated solutes improve bioavailability of the solute by about 1%, about 2%, about 3%, about 4%, about 5%, about 6%, about 7%, about 8%, or about 9%.

In some embodiments, the disclosure provides methods for improving the bioavailability of a solute, including, for example, dissolving the solute in ultrapure water and encapsulating the solute in a water cluster, wherein the water cluster has a median diameter between about 2 to about 400 nanometers. In further embodiments, the disclosure provides methods for improving the bioavailability of a small molecule drug, a protein, a peptide, a detoxification agent, a hydration agent, an anti-inflammatory agent, a neuroprotective agent, a neuromodulatory agent, or an anti-tumorigenic agent. In other embodiments, the disclosure provides methods for improving the bioavailability of an electrolyte solution, for example in a hydration, sports, or energy drink.

In some embodiments, the compositions having a solute encapsulated within a water cluster comprising or consisting essentially of ultrapure water have improved stability relative to compositions having the unencapsulated solute. In some embodiments, the solute encapsulated within a water cluster with improved stability has an increased half-life, such as an increased serum half-life or solution half-life. In some embodiments, the solute encapsulated within a water cluster comprising or consisting essentially of ultrapure water has improved stability for extended storage periods relative to the non-encapsulated solute.

In some embodiments, the compositions or solutions including water clusters comprising or consisting essentially of ultrapure water and a solute encapsulated within the water clusters have improved solubility relative to compositions or solutions including the unencapsulated solute. In other embodiments, a solute encapsulated in water clusters comprising or consisting essentially of ultrapure water comprises a drug with increased solubility, improved pharmacokinetics, and/or increased bioavailability. As such, embodiments of the disclosure have applications where improved solubility, pharmacokinetics, and/or bioavailability is desired, for example, without limitation, in medical products, patient care, medical research, medical testing, medical equipment, cell culture, and surgical procedures.

In some embodiments, the solute encapsulated within a water cluster normally has limited or no solubility in water but is solubilized when encapsulated in water clusters comprising or consisting essentially of ultrapure water. In alternative embodiments, the solute encapsulated within a water cluster may have low to moderate solubility in water but is solubilized (e.g., completely solubilized) when encapsulated in water clusters comprising or consisting essentially of ultrapure water.

In some embodiments, a solute of the disclosure further comprises a surface coating applied before or after encapsulating the solute in a water cluster comprising or consisting essentially of ultrapure water. For biological applications, such as proteins, the surface coating may be polar to give high aqueous solubility and prevent nanosized particle aggregation.

The disclosure also provides pharmaceutical compositions including water clusters comprising or consisting essentially of ultrapure water where the water clusters have a median water cluster diameter of between about 2 to about 400 nanometers and one or more active pharmaceutical ingredients encapsulated within the water clusters. In some embodiments, the active pharmaceutical ingredient is selected from a small molecule drug, a protein, a peptide, or a combination thereof. In other embodiments, the pharmaceutical ingredient is a cellular detoxification agent, a hydration agent, an anti-inflammatory agent, a neuroprotective agent, a neuromodulatory agent, or an anti-tumorigenic agent.

In some embodiments, the disclosure provides compositions or solutions used for delivering a therapeutic agent, medicament, drug, or the like, to a subject in need thereof. In some embodiments, an isotonic saline encapsulated in water clusters comprising or consisting essentially of ultrapure water is used for improving an for intravenous use in a mammal. In certain embodiments, a drug encapsulated in water clusters comprising or consisting essentially of ultrapure water is used to increase solubility of the drug. In certain embodiments, an oral drug encapsulated in water clusters comprising or consisting essentially of ultrapure water increases bioavailability of the oral drug. Furthermore, in certain embodiments, a drug encapsulated in water clusters comprising or consisting essentially of ultrapure water is used as a means for increasing potency of the drug.

In some embodiments, the compositions and solutions of the disclosure are suitable for oral or sublingual delivery, transdermal delivery, or delivery by inhalation (e.g., by nasal inhalation).

In some embodiments, a solute encapsulated in water clusters comprising or consisting essentially of ultrapure water is used for treating hypothermia in a mammal. In some embodiments, a solute encapsulated in water clusters comprising or consisting essentially of ultrapure water is used as a means for treating heat stroke in a mammal. In some embodiments, a solute encapsulated in water clusters comprising or consisting essentially of ultrapure water is useful as a means for treating shock from physical trauma in a mammal. In some embodiments, a solute encapsulated in water clusters comprising or consisting essentially of ultrapure water is used as a means for treating inflammation in a mammal. In still other embodiments, a drug encapsulated in water clusters comprising or consisting essentially of ultrapure water is used as a means for increasing drug potency.

In some embodiments, a solute encapsulated in water clusters comprising or consisting essentially of ultrapure water is used as a means for increasing potency and/or stability of a cancer drug. In certain embodiments, a solute encapsulated in a water cluster comprising or consisting essentially of ultrapure water is a peptide that interferes with the interaction between p53 and a MDM2 protein, e.g., a peptide corresponding to all or a portion of amino acid residues 12-26 of human p53 protein, For example, a solute encapsulated in a water cluster comprising or consisting essentially of ultrapure water comprises Vectcytotratin or PNC-28, as disclosed in U.S. Pat. Nos. 7,745,405 and 7,531,515, the contents of which are incorporated by reference herein in their entireties. Furthermore, in some embodiments, a solute encapsulated in water clusters comprising or consisting essentially of ultrapure water is used as a means for increasing Vectcytotratin potency, stability, and/or bioavailability.

In yet other embodiments, the disclosure provides a solute encapsulated in water clusters comprising or consisting essentially of ultrapure water as a means for increasing physical endurance in a mammal. For example, a solute encapsulated in water clusters comprising or consisting essentially of ultrapure water is used to increase endurance after prolonged physical exertion, such as aerobic and/or anaerobic exertion.

In some embodiments, the disclosure provides a solute encapsulated in water clusters comprising or consisting essentially of ultrapure water for increasing mental alertness or acuity in a mammal. In particular embodiments, a solute encapsulated in water clusters comprising or consisting essentially of ultrapure water is useful as a means for improving the mental thinking in a mammal. In embodiments, the disclosure provides a solute encapsulated in water clusters comprising or consisting essentially of ultrapure water to treat psychiatric conditions, such as depression, in a mammal.

In some embodiments, the present disclosure provides a drink (e.g., a hydration, sports, or energy drink) that includes a solute encapsulated in a water cluster comprising or consisting essentially of ultrapure water. In some embodiments, the solute comprises potassium chloride, vitamin B6, ferric chloride, magnesium sulfate, sodium chloride, Ionic Trace Minerals, kelp, taurine, alfalfa, or sodium borate. In other embodiments, the solute comprises capsaicin, resveratrol, quercetin, vitamin d3, and *Panax ginseng*. In still other embodiments, the solute comprises synapta, magnesium chloride, Concentrated Trace Minerals, and sodium benzoate. In some embodiments, the solute provides a means for increasing growth and body weight in mammals including humans and animals.

As used herein, Concentrated Trace Minerals comprise a plurality of the ions disclosed in Table 1 at the indicated concentration ranges:

TABLE 1

Concentrated Trace Mineral Solution Components

| Chemical Ion Species | Concentration |
|---|---|
| Aluminum | <10 micrograms/ml |
| Boron | 0.420-0.650 milligrams/ml |
| Calcium | <165 micrograms/ml |
| Chloride | 264-350 milligrams/ml |
| Copper | not established |
| Fluoride | <100 micrograms/ml |
| Iodine | <25 micrograms/ml |
| Iron | <31 micrograms/ml |
| magnesium | 101.5-110 milligrams/ml |
| Phosphorus | <10 micrograms/ml |
| Potassium | 1.25-2.5 milligrams/ml |
| Rubidium | <2 micrograms/ml |
| Silicon | <5 micrograms/ml |
| Sodium | <4 milligrams/ml |
| Sulfate | 16.5-35 milligrams/ml |
| Titanium | <4 micrograms/ml |
| Zinc | <3.5 micrograms/ml |
| Zirconium | <3.5 micrograms/ml |

In some embodiments, the solute is potassium, vitamin B6, iron, magnesium, chloride, sodium, ionic trace minerals, sulfate, kelp, taurine, alfalfa, or boron. In other embodiments, a hydration, sports, or energy drink is provided that comprises aluminum, boron, calcium, chloride, copper, fluoride, iodine, iron, magnesium, phosphorus, potassium, rubidium, silicon, sodium sulfate, titanium, zinc, or zirconium encapsulated in a water cluster comprising or consisting essentially of ultrapure water.

In a particular embodiment, the hydration, sports, or energy drink comprises potassium (e.g., 590 mg/50 gallons), vitamin b6 (e.g., 2 mg/50 gallons), iron (e.g., 5 mg/50 gallons), magnesium (e.g., 265 mg/50 gallon), chloride (e.g., 279 mg/50 gallons), sodium (e.g., 270 mg/50 gallons), ionic trace minerals (e.g., 10.530 g/50 gallons), sulfate (e.g., 110 mg/50 gallons), kelp (e.g., 100 mg/50 gallons), taurine (e.g., 100 mg/50 gallons), alfalfa (e.g., 50 mg/50 gallons), and/or boron (e.g., 2 mg/50 gallons).

In yet another embodiment, the disclosure provides a hydration, sports, or energy drink, wherein an about 8 ounce solution of the hydration, sports, or energy drink comprises a carbohydrate (e.g., 4.1 mg), a sugar (e.g. glucose, sucrose, fructose, maltose, or another hexose sugar) (e.g., 4.1 mg glucose), vitamin c (citrate) (e.g., 0.027 mg), a magnesium cation (e.g., 0.068 mg), a chloride anion (e.g., 0.23 mg), a sodium cation (e.g., 0.0045 mg), a potassium cation (e.g., 0.045 mg), a sulfate anion (e.g., 0.011 mg), and/or boron (e.g., 0.36 micrograms).

In yet another embodiment, the disclosure provides a hydration, sports, or energy drink including water clusters comprising or consisting essentially of ultrapure water, and Concentrace Trace Mineral Drops™, Himalayan Pink Salt, 40K Volts Electrolyte Concentrate™ (dietary supplement made by Trace Minerals, Utah.), and/or sodium bicarbonate, wherein the Concentrace Trace Mineral Drops™, Himalayan Pink Salt, 40K Volts Electrolyte Concentrate™ (dietary supplement made by Trace Minerals, Utah.), and/or sodium bicarbonate are encapsulated by the water clusters. In a particular embodiment, the disclosure provides a hydration, sports, or energy drink comprising water clusters comprising or consisting essentially of ultrapure water (e.g., 50 gallons), Trace Mineral Drops™ (e.g., 0.1-0.8 oz/50 gallons), Himalayan Pink Salt (e.g., 25-950 mg/50 gallons), sodium bicarbonate (e.g., 1-12 oz/50 gallons), and/or 40K Volts Electrolyte Concentrate™ (e.g., 1-6 oz/50 gallons), wherein the Trace Mineral Drops™, Himalayan Pink Salt, sodium bicarbonate, and/or 40K Volts Electrolyte Concentrate™ are encapsulated by the water clusters.

In yet another embodiment, the disclosure provides a hydration, sports, or energy drink comprising water clusters comprising or consisting essentially of ultrapure water and a solute, wherein the water clusters encapsulate the solute, and wherein the solute comprises a combination of ions (e.g., cations or ions). In some embodiments, the ion is selected from the group consisting of an aluminum cation, an antimony cation, an arsenic cation, a barium cation, a beryllium cation, a bismuth cation, a boron ion, a bromide anion, a cadmium cation, a calcium cation, a cerium cation, a cesium cation, a chloride anion, a chromium cation, a cobalt cation, a copper cation, a dysprosium cation, an erbium cation, a europium cation, a fluoride anion, a gadolinium cation, a gallium cation, a germanium cation, a gold cation, a hafnium cation, a holmium cation, an indium cation, a iodine anion, an iridium cation, an iron cation, a lanthanum cation, a lead cation, a lithium cation, a lutetium cation, a magnesium cation, a manganese cation, a mercury cation, a molybdenum cation, a neodymium cation, a nickel cation, a niobium cation, an osmium cation, a palladium cation, a phosphorus anion, a platinum cation, a potassium cation, a praseodymium cation, a rhenium cation, a rhodium cation, a rubidium cation, a ruthenium cation, a samarium cation, a scandium cation, a selenium cation, a silicon cation, a silver cation, a sodium cation, a strontium cation, a sulfate anion, a tantalum cation, a tellurium cation, a terbium cation, a thallium cation, a thorium cation, a thulium cation, a tin cation, a titanium cation, a tungsten cation, a vanadium cation, a ytterbium cation, a yttrium cation, a zinc cation, and a zirconium cation.

In alternative embodiments, the ion is selected from the group consisting of aluminum cation, an antimony cation, a barium cation, a bismuth cation, a boron ion, a bromide anion, a calcium cation, a cerium cation, a cesium cation, a chloride anion, a chromium cation, a cobalt cation, a copper cation, a dysprosium cation, an erbium cation, a europium cation, a fluoride anion, a gadolinium cation, a gallium cation, a germanium cation, a gold cation, a hafnium cation, a holmium cation, an indium cation, a iodine anion, an iridium cation, an iron cation, a lithium cation, a lutetium cation, a magnesium cation, a manganese cation, a molybdenum cation, a neodymium cation, a niobium cation, an osmium cation, a palladium cation, a phosphorus anion, a platinum cation, a potassium cation, a praseodymium cation, a rhenium cation, a rhodium cation, a rubidium cation, a ruthenium cation, a samarium cation, a scandium cation, a selenium cation, a silicon cation, a silver cation, a sodium cation, a strontium cation, a sulfate anion, a tantalum cation, a tellurium cation, a terbium cation, a thulium cation, a tin cation, a titanium cation, a tungsten cation, a vanadium cation, a ytterbium cation, a yttrium cation, a zinc cation, and a zirconium cation.

In still other embodiments, the ion is selected from the group consisting of an antimony cation, a barium cation, a bismuth cation, a boron ion, a bromide anion, a calcium cation, a cerium cation, a chloride anion, a chromium cation, a cobalt cation, a copper cation, a europium cation, a fluoride anion, a gold cation, a iodine anion, an iron cation, a lithium cation, a magnesium cation, a manganese cation, a molybdenum cation, a an osmium cation, a palladium cation, a phosphorus anion, a platinum cation, a potassium cation, a rubidium cation, a ruthenium cation, a scandium cation, a selenium cation, a silicon cation, a silver cation, a sodium cation, a strontium cation, a sulfate anion, a tantalum cation, a tin cation, a titanium cation, a tungsten cation, a vanadium cation, and a zinc cation.

The disclosure further provides a hydration, sports, or energy drink for establishing or maintaining a healthy body weight, for increasing or maintaining metabolism, for increasing or maintaining energy levels, for reducing pain, for reducing joint or back pain, for improved flushing of body waste, for treating or preventing headaches, for alleviating headache symptoms, for improving skin hydration and skin health, and/or for reducing the effects of aging.

The present disclosure also provides a solute encapsulated in water clusters comprising or consisting essentially of ultrapure water wherein the solute is capable of lessening mortality in mammals including humans and animals. In addition, embodiments of the disclosure provide a solute encapsulated in water clusters comprising or consisting essentially of ultrapure water used for increasing a mammal's recovery from dehydration.

In still other embodiments, the disclosure provides a composition or solution for improving, enhancing, or restoring immune function. In some embodiments, the composition or solution for improving enhancing, or restoring immune function comprise water clusters comprising or consisting essentially of ultrapure water that stably encapsulate a solute selected from capsaicin, quercetin, vitamin d3, and *Panax ginseng*.

In a particular embodiment, the disclosure provides a composition or solution for improving enhancing, or restoring immune function that includes water clusters comprising or consisting essentially of ultrapure water, and capsaicin (e.g., 42.5 g/50 gallons), trans-resveratrol (e.g., 700 mg/50 gallons), quercetin (e.g., 100 mg/50 gallons), vitamin d3 (e.g., 5000 mg/50 gallons), and/or *Panax ginseng* (e.g., 400 mg/50 gallons), wherein the water clusters encapsulate the capsaicin, trans-resveratrol, quercetin, vitamin d3, and/or *Panax ginseng*.

In yet further embodiments, the disclosure provides a composition or a solution for treating erectile dysfunction. In some embodiments, the composition or solution targeting erectile function comprise water clusters comprising or consisting essentially of ultrapure water that stably encapsulate a solute selected from L-arginine, horny goat weed, *Mondia whitei*, pine pollen, longjack, *Panax ginseng*, yohimbine, and/or *Tribulus terrestris*.

In a particular embodiment, the disclosure provides a composition or solution for treating erectile dysfunction that includes water clusters comprising or consisting essentially of ultrapure water, and L-arginine (e.g., 6 g/50 gallons), horny goat weed (e.g., 1.5 g/50 gallons), *Mondia whitei* (e.g., 450 mg/50 gallons), pine pollen (e.g., 5 g/50 gallons), longjack (e.g., 600 mg/50 gallons), *Panax ginseng* (e.g., 400 mg/50 gallons), yohimbine (e.g., 18 mg/50 gallons), and/or *Tribulus terrestris* (e.g., 400 mg/50 gallons), wherein the water clusters encapsulate the L-arginine, horny goat weed, *Mondia whitei*, pine pollen, longjack, *Panax ginseng*, yohimbine, and/or *Tribulus terrestris*.

In still further embodiments, the disclosure provides a composition or solution for promoting or enhancing weight loss that includes water clusters comprising or consisting essentially of ultrapure water that stably encapsulate a solute selected from moringa, MCT (medium-chain triglycerides), saffron, naringin, greenselect phytosome, curcumin, *Panax ginseng*, forskolin, and/or niacin.

In a particular embodiment, the disclosure provides a composition or solution for promoting or enhancing weight loss that includes water clusters comprising or consisting essentially of ultrapure water, and moringa (e.g., 500 mg/50 gallons), MCT (e.g., 4 g/50 gallons), saffron (e.g., 15 mg/50 gallons), naringin (e.g., 500 mg/50 gallons), greenselect phytosome (e.g., 400 mg/50 gallons), curcumin (e.g., 250 mg/50 gallons), *Panax ginseng* (e.g., 400 mg/50 gallons), forskolin (e.g., 500 mg/50 gallons), and/or niacin (e.g., 500 mg/50 gallons), wherein the water clusters encapsulate the L-arginine, horny goat weed, *Mondia whitei*, pine pollen, longjack, *Panax ginseng*, yohimbine, and/or *Tribulus terrestris*.

In other embodiments, the disclosure provides an anti-aging composition or solution that includes water clusters comprising or consisting essentially of ultrapure water that stably encapsulate a solute selected from multi 5 collagen, MCT, silicon, choline, nicotinamide riboside, trans-resveratrol, pterostilbene, b vitamin complex, vitamin c, and/or niacin.

In a particular embodiment, the disclosure provides an anti-aging composition or solution that includes water clusters comprising or consisting essentially of ultrapure water, and multi 5 collagen (e.g., 7.8 g/50 gallons), silicon (ch-osa) (e.g., 10 mg/50 gallons), choline (ch-osa) (e.g., 10 mg/50 gallons), nad+(nicotinamide riboside) (e.g., 1000 mg/50 gallons), trans-resveratrol (e.g., 500 mg/50 gallons), pterostilbene (e.g., 400 mg/50 gallons), b vitamin complex (e.g., 400 mg/50 gallons), vitality c-(vitamin c) (e.g., 4 g/50 gallons), and/or niacin (e.g., 500 mg/50 gallons), wherein the water clusters encapsulate the L-arginine, horny goat weed, *Mondia whitei*, pine pollen, longjack, *Panax ginseng*, yohimbine, and/or *Tribulus terrestris*.

In still other embodiments, the disclosure provides a composition or solution for treating, ameliorating, preventing, or managing the symptoms of diabetic neuropathy that includes water clusters comprising or consisting essentially of ultrapure water that stably encapsulate a solute selected from R-ala, thiamine (b1)-, riboflavin (b2), niacin, vitamin, folate, vitamin (b12), biotin, pantothenic acid, calcium, inositol, paba, acetyl-1-carnitine, gla, chromium, curcumin, vitamin c, vitamin e, magnesium malate, cordyalis, cayenne (only 40,000 h.u.), 1 arginine, and/or feverfew.

In a particular embodiment, the disclosure provides a composition or solution for treating, ameliorating, preventing, or managing the symptoms of diabetic neuropathy comprising water clusters comprising or consisting essentially of ultrapure water, and r-ala (e.g., 100 mg/50 gallons), thiamine (b1) (e.g., 100 mg/50 gallons), riboflavin (b2) (e.g., 75 mg/50 gallons), niacin (e.g., 100 mg/50 gallons), vitamin (e.g., 100 mg/50 gallon), folate (e.g., 400 mg/50 gallons), vitamin (b12) (e.g., 300 mcg/50 gallons), biotin (e.g., 1000 mg/50 gallons), pantothenic acid (e.g., 500 mg/50 gallons), calcium (e.g., 60 mg/50 gallons), inositol (e.g., 100 mg/50 gallons), paba (e.g., 50 mg/50 gallons), acetyl-1-carnitine (e.g., 1000 mg/50 gallons), gla (e.g., 299 mg/50 gallons), chromium (e.g., 500 mg/50 gallons), curcumin (e.g., 250 mg/50 gallons), vitamin c (e.g., 4000 mg (6.5 g)/50 gallons), vitamin e (e.g., 1000 mg/50 gallons), magnesium malate (e.g., 210 mg/50 gallons), corydalis (e.g., 1000 mg/50 gallons), cayenne (only 40,000 h.u.) (e.g., 500 mg/50 gallons), 1 arginine (e.g., 6 g/50 gallons), and/or feverfew (e.g., 600 mg/50 gallons), wherein the water cluster encapsulate the r-ala (100 mg/50 gallons), thiamine (b1) (100 mg/50 gallons), riboflavin (b2) (75 mg/50 gallons), niacin 100 mg/50 gallons), vitamin (100 mg/50 gallon), folate (400 mg/50 gallons), vitamin (b12) (300 mcg/50 gallons), biotin (1000 mg/50 gallons), pantothenic acid (500 mg/50 gallons), calcium (60 mg/50 gallons), inositol (100 mg/50 gallons), paba (50 mg/50 gallons), acetyl-1-carnitine (1000 mg/50 gallons), gla (299 mg/50 gallons), chromium (500 mg/50 gallons), curcumin (250 mg/50 gallons), vitamin c (4000 mg (6.5 g)/50 gallons), vitamin e (1000 mg/50 gallons), magnesium malate (210 mg/50 gallons), corydalis (1000 mg/50 gallonsm), cayenne (only 40,000 h.u.) (500 mg/50 gallons), 1 arginine (6 g/50 gallons), and/or feverfew (600 mg/50 gallons).

In yet further embodiments, the disclosure provides a composition or solution for treating diabetic blood sugar disorder that includes water clusters comprising or consisting essentially of ultrapure water that stably encapsulate a solute selected from berberine, zychrome, *Gymnema sylvestre*, ala, cinnamon, *Panax ginseng*, magnesium, fenugreek, and/or niacin.

In a particular embodiment, the disclosure provides a composition or solution for treating diabetic blood sugar disorder comprising water clusters comprising or consisting essentially of ultrapure water, and berberine hcl (e.g., 500 mg/50 gallons), zychrome (chromium), (e.g., 1000 mg/50 gallons), *Gymnema sylvestre* (e.g., 250 mg/50 gallons), ala (e.g., 100 mg/50 gallons), cinnamon (e.g., 2 g/50 gallons), *Panax ginseng* (e.g., 400 mg/50 gallons), magnesium (e.g., 500 mg/50 gallons), fenugreek (e.g., 1260 mg/50 gallons), and/or niacin (e.g., 100 mg/50 gallons), wherein the water clusters encapsulate the berberine hcl (500 mg/50 gallons), zychrome (chromium), (1000 mg/50 gallons), *Gymnema sylvestre* (250 mg/50 gallons), ala (100 mg/50 gallons), cinnamon (2 g/50 gallons), *Panax ginseng* (400 mg/50 gallons), magnesium (500 mg/50 gallons), fenugreek (1260 mg/50 gallons), and/or niacin (100 mg/50 gallons).

In still further embodiments, the disclosure provides a composition or solution for treating, ameliorating, preventing, or managing the symptoms of anxiety disorder that includes water clusters comprising or consisting essentially of ultrapure water that encapsulates a solute selected from 40K Volts Electrolyte Concentrate, CBD, sodium bicarbonate, sodium benzoate, and/or Concentrated Trace Mineral.

In particular embodiments, the disclosure provides a composition for treating, ameliorating, preventing, or managing the symptoms of anxiety disorder comprising water clusters comprising or consisting essentially of ultrapure water (300 gallons) and CBD (e.g. 0.005-300 g), Trace Mineral Drops™ (e.g. between 0.001-10.8 liters), 40K Volts Electrolyte Concentrate™ 40K (e.g. between 0.001-6.9 liters), sodium bicarbonate (e.g. between 1-360 grams), and/or sodium benzoate (e.g. between 0.01-240 grams), wherein the water clusters encapsulate the CBD (0.005-300 g), Trace Mineral Drops™ (between 0.001-10.8 liters), 40K Volts Electrolyte Concentrate™ 40K (between 0.001-6.9 liters), sodium bicarbonate (between 1-360 grams), and/or sodium benzoate (between 0.01-240 grams.

In embodiments, the disclosure provides a composition or solution that includes a solute encapsulated by a water cluster comprising or consisting essentially of ultrapure water, wherein the solute is selected from any of the diverse chemical compounds that act on cannabinoid receptors on cells in the brain, or act on orthosteric or allosteric sites and modulate endocannabinoid activity. Accordingly, embodiments provide cannabinoid receptor compounds including, without limitation, the phytocannabinoids found in *Cannabis*, hempseed oil, other plants, and synthetic cannabinoids manufactured artificially. They include the phytocannabinoids delta-9-tetrahydrocannabinol (THC), cannabidiol (CBD), cannabinol (CBN) cannabigerol (CBG), cannabigerol (CBG), eannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM), or the like; or mixtures or combinations thereof. Other botanical cannabimimetics include N-alkylamides from *Echinacea* and B-caryophyllene. Further embodiments provide cannabinoid receptor compounds including, without limitation, mixtures of phytocannabinoids separated from the plant by extraction techniques and high purity cannabinoids obtained by purification from natural sources or via synthesis.

In further particular embodiments, the disclosure provides a composition or solution that includes a solute encapsulated in water clusters comprising or consisting essentially of ultrapure water for enhancing, improving, restoring, or treating neurological function, wherein the solute is Synapta (SynaptaGenX™ dietary supplement); a magnesium salt;

Concentrace Trace Mineral Drops™; and/or sodium benzoate. For example, to 300 gallons of ultrapure water may be added the following brain health formulation ingredients: about 0.001-1000 grams of Synapta™; about 0.01-3000 grams of magnesium chloride; about 0.08-3.8 liters of Trace Mineral Drops™; and/or about 0.01-240 grams of sodium benzoate.

In further particular embodiments, the disclosure provides a composition or solution for treating Dyspepsia comprising a solute encapsulated in water clusters comprising or consisting essentially of ultrapure water, wherein the solute is Bio Nutrition Gout Out™ (Goutout is by BIO Nutrition a dietary supplement), Tart Cherry, and/or sodium benzoate.

In a particular embodiment, the disclosure provides a composition (e.g., a pharmaceutical formulation) or solution for treating Dyspepsia that includes water clusters comprising or consisting essentially of ultrapure water (e.g., 50 gallons), and Bionutrition Gout Out™ (e.g., 1-8 caps/50 gallons), Tart Cherry (e.g., 1-4 caps/50 gallons), and/or sodium benzoate (e.g., 0.4-4 oz/50 gallons), wherein the water clusters encapsulate the Bionutrition Gout Out™ (1-8 caps/50 gallons), Tart Cherry (1-4 caps/50 gallons), and/or sodium benzoate (0.4-4 oz/50 gallons).

In further particular embodiments, the disclosure provides a composition or solution for treating headaches that includes a solute encapsulated in water clusters comprising or consisting essentially of ultrapure water, wherein the solute comprises Resveratrol™, Liver Care™, D-Ribose, 40K Volts Electrolyte Concentrate™, Concentrated Trace Mineral Drops™, and/or sodium benzoate.

In particular embodiments, the disclosure provides a composition or solution for treating headaches that includes water clusters comprising or consisting essentially of ultrapure water (e.g., 50 gallons), and Resveratrol™ (e.g., 0.5 pill 10 mg/50 gallons), Liver Care™ (e.g., 0.10-0.80 mg/50 gallons), D-ribose (e.g., 0.1-0.6 mg/50 gallons), 40K Electrolyte Concentrate™ (e.g., 1-4 oz/50 gallons), Trace Mineral Drops™ (e.g., 10-120 drops/50 gallons), and/or sodium benzoate (e.g., 0.2-1 oz/50 gallons), wherein the water cluster encapsulate the Resveratrol™ (0.5 pill 10 mg/50 gallons), Liver Care™ (10-0.80 mg/50 gallons), D-ribose (0.1-0.6 mg/50 gallons), 40K Electrolyte Concentrate™ (1-4 oz/50 gallons), Trace Mineral Drops™ (10-120 drops/50 gallons), and/or sodium benzoate (0.2-1 oz/50 gallons).

In further particular embodiments, the disclosure provides a composition or solution for treating the common cold that includes a solute encapsulated in water clusters comprising or consisting essentially of ultrapure water, wherein the solute comprises CBD, capsaicin, Concentrace Trace Mineral Drops™, Resveratrol™, and/or sodium benzoate.

In particular embodiments, the disclosure provides a cold remedy composition or solution that includes water clusters comprising or consisting essentially of ultrapure water (e.g., 50 gallons), and capsaicin (e.g., 1-4 ozs/50 gallons), CBD (e.g., 0.1-2 g/50 gallons), Trace Mineral Drops™ (e.g., 0.2-0.6 oz/50 gallons), Resveratrol™ (e.g., 0.1-2 mg/50 gallons), and/or sodium benzoate (e.g., 0.1-5 oz/50 gallons), wherein the water clusters encapsulate the capsaicin (1-4 ozs/50 gallons), CBD (0.1-2 g/50 gallons), Trace Mineral Drops™ (0.2-0.6 oz/50 gallons), Resveratrol™ (0.1-2 mg/50 gallons), and/or sodium benzoate (0.1-5 oz/50 gallons).

In further particular embodiments, the disclosure provides a composition or solution for elder care that includes a solute encapsulated in water clusters comprising or consisting essentially of ultrapure water, wherein the solute comprises Multi 5 Collagen™, Silicon/Choline™ (ch-OSA), nicotinamide riboside, Trans-Resveratrol, B vitamin complex, vitamin C, and/or sodium benzoate.

In particular embodiments, the disclosure provides an elder care composition or solution that include water clusters comprising or consisting essentially of ultrapure water, (e.g., 50 gallons), and Multi 5 Collagen™ (e.g., 0.5-4 g/50 gallons), Silicon/Choline™ (e.g., 2-12 drops/50 gallons), nicotinamide riboside (e.g., 0.25-1.25 tabs/50 gallons) (Note FDA Ingredient Naigin), Trans Resveratrol™ (e.g., 0.1-1 cap/50 gallons), B vitamin complex (e.g., 0.5-3 cap/50 gallons), and/or vitamin C (e.g., 1-4 g/50 gallons), wherein the water clusters encapsulate the Multi 5 Collagen™ (0.5-4 g/50 gallons), Silicon/Choline™ (2-12 drops/50 gallons), nicotinamide riboside (0.25-1.25 tabs/50 gallons) (Note FDA Ingredient Naigin), Trans (Resveratrol™ (0.1-1 cap/50 gallons), B vitamin complex (0.5-3 cap/50 gallons), and/or vitamin C (1-4 g/50 gallons).

In further particular embodiments, the disclosure provides a composition or solution for diabetic binge that includes a solute encapsulated in water clusters comprising or consisting essentially of ultrapure water, wherein the solute comprises Berberine HCL™, Zychrome™ Gymnema Sylvestre™ (Organix Glucose Gymnema Elite by Nutrusta), R-alpha lipoic Acid (R-ALA), cinnamon, Panax ginseng™ (Fermented Korean Panax ginseng), magnesium, and/or Fenugreek™.

In particular embodiments, the disclosure provides a diabetic binge composition or solution that includes water clusters comprising or consisting essentially of ultrapure water (e.g., 50 gallons), and Berberine HCL™ (e.g., 200-700 mg/50 gallons), Zychrome™ (e.g., 10-150 mcg/50 gallons), Gymnema Sylvestre™ (e.g., 12-140 mg/50 gallons), ALA (e.g., 2-30 mg/50 gallons), cinnamon (e.g., 0.1-4.0 g/50 gallons), Panax ginseng™ (e.g., 10-110 mg/50 gallons), magnesium (e.g., 10-200 mg/50 gallons), and/or Fenugreek™ (e.g., 3-400 mg/50 gallons), wherein the water clusters encapsulate the Berberine HCL™ (200-700 mg/50 gallons), Zychrome™ (10-150 mcg/50 gallons), Gymnema Sylvestre™ (12-140 mg/50 gallons), ALA (2-30 mg/50 gallons), cinnamon (0.1-4.0 g/50 gallons), Panax ginseng™ (10-110 mg/50 gallons), magnesium (10-200 mg/50 gallons), and/or Fenugreek™ (3-400 mg/50 gallons).

In further particular embodiments, the disclosure provides a composition or solution for reflex neurology that includes a solute encapsulated in a water cluster comprising or consisting essentially of ultrapure water, wherein the solute comprises a R-ALA (Alpha Lipoic Acid), B-Complex, acetyl-L-carnitine, GLA (Gamma Linolenic Acid), chromium, curcumin, vitamin c, vitamin e, vitamin k2 & d3, magnesium, corydalis, cayenne, 1-arginine, Feverfew™ (Tanacetum Parthenium), and/or sodium benzoate.

In particular embodiments, the disclosure provides a reflex neurology composition or solution that includes water clusters comprising or consisting essentially of ultrapure water (e.g., 50 gallons), and R-ALA (e.g., ⅒-½ capsule/50 gallons), acetyl-L-carnitine (e.g., 50-280 mg/50 gallons), GLA (e.g., 50-400 mg/50 gallons), chromium (e.g., 25-125 mcg/50 gallons), curcumin 20 (e.g., 160 mg/50 gallons), vitamin C (e.g., 200-2000 mg/50 gallons), vitamin K-2 & D-3 (e.g., 25-100 mcg/50 gallons), magnesium (e.g., 20-120 mg/50 gallons), corydalis (e.g., 125-375 mg/50 gallons), cayenne (e.g., 10-150 mg/50 gallons), L-arginine (e.g., 60-1000 mg/50 gallons), Feverfew™ (e.g., 10-120 mg/50 gallons), and/or sodium benzoate (e.g., 0.1-2.0 ozs), wherein the water clusters encapsulate the R-ALA (⅒-½ capsule/50 gallons), acetyl-L-carnitine (50-280 mg/50 gallons), GLA (50-400 mg/50 gallons), chromium (25-125 mcg/50 gallons), curcumin 20 (160 mg/50 gallons), vitamin C (200-2000 mg/50 gallons), vitamin K-2 & D-3 (25-100 mcg/50 gallons), magnesium (20-120 mg/50 gallons), corydalis (125-375 mg/50 gallons), cayenne (10-150 mg/50 gallons), L-arginine (60-1000 mg/50 gallons), Feverfew™ (10-120 mg/50 gallons), and/or sodium benzoate (0.1-2.0 ozs).

In further particular embodiments, the disclosure provides a composition or solution for treating erectile dysfunction that includes a solute encapsulated in water clusters comprising or consisting essentially of ultrapure water, wherein the solute comprises 1-arginine, horny goat weed, *mondia whitei*, Long Jack™, *Panax ginseng*, yohimbine (from libido health is a common plank alkaloid), *Tribulus terrestris*, tadalafil, and/or sodium benzoate.

In particular embodiments, the disclosure provides an erectile dysfunction composition or solution that includes water clusters comprising or consisting essentially of ultrapure water (e.g., 50 gallons), and L-arginine (e.g., 5.5-25 g/50 gallons), Horny Goat Weed (e.g., 1.5-7 g/50 gallons), *Mondia Whitei* (e.g., 10-450 mg/50 gallons), Long Jack™ (e.g., 2-300 mg/50 gallons), *Panax Ginseng*™ (e.g., 10-345 mg/50 gallons), Yohimbine (e.g., 0.1-10 mg/50 gallons), *Tribulus Terrestris* (e.g., 10-140 mg/50 gallons), Tadalafil (e.g., 5-40 mg/50 gallons), and/or sodium benzoate (e.g., 0.3-0.9 ozs/50 gallons), wherein the water clusters encapsulate the L-arginine (5.5-25 g/50 gallons), Horny Goat Weed (1.5-7 g/50 gallons), *Mondia Whitei* (10-450 mg/50 gallons), Long Jack™ (2-300 mg/50 gallons), *Panax ginseng*™ (10-345 mg/50 gallons), Yohimbine (0.1-10 mg/50 gallons), *Tribulus Terrestris* (10-140 mg/50 gallons), Tadalafil (5-40 mg/50 gallons), and/or sodium benzoate (0.3-0.9 ozs/50 gallons).

In further particular embodiments, the disclosure provides a composition or solution for central nervous system wellness that includes a solute encapsulated in water clusters comprising or consisting essentially of ultrapure water, wherein the solute comprises caffeine, theanine, b6 complex, *Ginkgo biloba*, curcumin, Huperzine A™, cognizine Citicoline™, 40 k volts electrolyte Concentrate™, Concentrace Trace Mineral Drops™, medium chain triglyceride oil powder, nicotinomide riboside, *rhodiola*, ketone esters, Resveratrol™, and/or sodium benzoate.

In particular embodiments, the disclosure provides a CNS wellness composition or solution that includes water clusters comprising or consisting essentially of ultrapure water (e.g., 100 gallons), and caffeine (e.g., 0.25-6 mg/100 gallons), theanine (e.g., 125-400 mg/100 gallons), B 6 Complex (e.g., 250-0.500 mg/50 gallons), *Ginkgo biloba* (e.g., 0 10-30 mg/50 gallons), curcumin (e.g., 625 mg/50 gallons), Huperzine A™ (e.g., 150-175 mg/50 gallons), Cognizine Citicoline™ (e.g., 0.07-0.9 mg/50 gallons), 40K Volts Electrolyte Concentrate™ (e.g., 1-5 ozs/50 gallons), Trace Mineral Drops™ (e.g., 0.2-0.8 ozs/50 gallons), MCT Oil Powder™ (e.g., 2-4 g/50 gallons), nicotinomide riboside (e.g., 100-200 mg/50 gallons), *rhodiola* (e.g., 0.3-0.6 ml (two full drop)/50 gallons), Ketone Esters (e.g., 4.7 g/50 gallons), Resveratrol™ (e.g., 12-36 mg/50 gallons), and/or sodium benzoate (e.g., 0.9 ozs/50 gallons), wherein the water clusters encapsulate the caffeine (0.25-6 mg/100 gallons), theanine (125-400 mg/100 gallons), B 6 Complex (250-0.500 mg/50 gallons), *Ginkgo biloba* (10-30 mg/50 gallons), curcumin (0.625 mg/50 gallons), Huperzine A™ (150-175 mg/50 gallons), Cognizine Citicoline™ (0.07-0.9 mg/50 gallons), 40K Volts Electrolyte Concentrate™ (1-5 ozs/50 gallons), Trace Mineral Drops™ (0.2-0.8 ozs/50 gallons), MCT Oil Powder™ (2-4 g/50 gallons), nicotinomide riboside (100-200 mg/50 gallons), *rhodiola* (0.3-0.6 ml (two full drop)/50 gallons), Ketone Esters (4.7 g/50 gallons), Resveratrol™ (12-36 mg/50 gallons), and/or sodium benzoate (0.9 ozs/50 gallons).

The disclosure also provides compositions and solutions for use in agricultural applications. In some embodiments, the disclosure provides compositions or solutions for use in fertilizer delivery, soil or plant hydration, heat tolerance, or seed germination. In further embodiments, the disclosure provides compositions or solutions for use in livestock management, such as livestock feed or drug administration.

In still other embodiments, the disclosure provides a composition or solution that includes a solute encapsulated in a water cluster comprising or consisting essentially of ultrapure water, wherein the solute comprises a plant or crop fertilizer. In some embodiments, the solute is used for increasing root development in plants, to increase leaf development in plants, for increasing water uptake in plants, for increasing drought tolerance in plants, for increasing crop yields in plants, for increasing the rate of tree growth, for increasing fruit production from trees, for improving sweetness of grapes on grape vines, and/or to generally improve the quality of agricultural products.

In certain embodiments, the solute is selected from nitrogen, phosphorous, potassium, calcium, magnesium, ammonium, sulfur, copper, iron, manganese, molybdenum, zinc, boron, silicon, cobalt, vanadium and/or urea. In certain embodiments, the solute comprises a plant nutritional agent.

In some embodiments, the disclosure provides compositions or solutions that include water clusters comprising or consisting essentially of ultrapure water and an encapsulated solute for improving the health and lifespan of livestock. Embodiments of the disclosure are useful for improving the health and lifespan of domesticated mammals and livestock. In embodiments, the disclosure provides compositions or solutions useful for improving the health and lifespan of, without limitation, cattle, swine, lamb, horses. Further embodiments of the disclosure are useful for improving the health and lifespan of, without limitation, poultry or fish. In other embodiments, the disclosure provides compositions or solutions useful for improving the health and lifespan of deer, elk, bison sheep, deer, ostrich, emu, llama and alpaca. In still further embodiments, the disclosure provides compositions and solutions useful for immune enhancement of livestock.

In further particular embodiments, the disclosure provides agricultural compositions or solutions comprising a solute encapsulated in a water cluster comprising or consisting essentially of ultrapure water, wherein the solute comprises Fulvic Humic Liquid.

In particular embodiments, the disclosure provides a CNS wellness composition or solution that includes water clusters comprising or consisting essentially of ultrapure water (e.g., 275 gallons) and Fulvic Humic liquid (e.g., 5-25 ozs/275 gallons), wherein the water clusters encapsulate the Fulvic Humic liquid.

The present disclosure also provides a process of making water clusters comprising or consisting essentially of ultrapure water that encapsulate a solute, wherein the solute is added to ultrapure water (e.g., 50 gallons) and wherein the solute is potassium chloride (e.g. between about 10 to 1200 milligrams), vitamin B6 (e.g. between about 0.0017 to 500 milligrams), ferric chloride (e.g. between about 0.001 to 100 milligrams), magnesium sulfate (e.g. between about 0.0011 to 800 milligrams), sodium chloride (e.g. between about 0.6 to 5000 milligrams); Ionic Trace Minerals (e.g. between about 0.5 to 75 grams), kelp (e.g. between about 1.1 to 1000 milligrams), taurine (e.g. between about 10-500 milligrams), alfalfa (e.g. between about 5.4 to 100 milligrams), and/or sodium borate (e.g. between about 0.0022 to 60 milligrams).

In some embodiments, the present disclosure also provides a process of making water clusters comprising or consisting essentially of ultrapure water that encapsulate a solute, wherein the solute is added to ultrapure water (e.g., 50 gallons), and wherein the solute is capasaicin (e.g., between about 0.02 ozs. to 25 ozs.), resveratrol (e.g. between about 0.05 milligrams to 16 milligrams), quercetin (e.g. between about 10 milligrams to 850 milligrams), vitamin D3 (e.g. between about 500 milligrams to 12,000 milligrams), and/or *Panax ginseng* (between about 4 milligrams to 4,000 milligrams).

In some embodiments, the present disclosure also provides a process of making water clusters comprising or consisting essentially of ultrapure water that encapsulate a solute, wherein the solute is added to ultrapure water (e.g., 50 gallons), and wherein the solute is Synapta (e.g. between about 0.001 grams to 1000 grams), magnesium chloride (e.g. between about 0.001 grams to 3000 grams); Concentrace Trace Mineral Drops (e.g. between about 0.0001 liters to 3 liters), and/or sodium benzoate (e.g., between about 0.01 grams to 100).

In some embodiments, the disclosure provides a process of making water clusters comprising or consisting essentially of ultrapure water that encapsulates a solute, comprising the following solutes added to a volume of 50 gallons of ultrapure water: Synapta (e.g. between about 0.001 grams to 1000 grams); of magnesium chloride (e.g. between about 0.001 grams to 3000 grams), Concentrace Trace Mineral Drops (e.g. between about 0.0001 liters to 3 liters), and/or sodium benzoate (e.g., between about 0.01 grams to 100 grams).

Embodiments of the present disclosure can be used in the pharmaceutical industry or may be used as a source of water for a pharmaceutical use, manufacturing of pharmaceutical products, medical devices, biologics, cell- and tissue-based products, and other medical products.

The present disclosure also provides methods for encapsulating a solute in a water cluster comprising or consisting essentially of ultrapure water.

In some embodiments, the disclosure provides a process for encapsulating a solute in a water cluster comprising or consisting essentially of ultrapure water comprising: selecting an amount of solute to add to a volume of ultrapure water; combining the solute and ultrapure water in a mixing tank to form a blended aqueous composition; pumping the blended aqueous composition at a selected flow rate through a transfer pipe from the mixing tank to a nozzle with one jet opening or a plurality of jet openings inside a hollow cylinder; using the one jet opening or the plurality of jet openings in the nozzle to jet the blended aqueous composition into the hollow cylinder; wherein the selected flow rate creates a vortex of the blended aqueous composition inside the hollow cylinder that encapsulates the solutes and reduce sizes of the water clusters in the blended aqueous composition. The process according to certain embodiments may further comprise collecting the composition comprising the encapsulated solute in the reduced size water clusters; and using the reduced size water clusters containing the solute to improve the bioavailability of the solute.

In some embodiments, a process is provided for reducing the size of water clusters in a solution of ultrapure water substantially free of dissolved solutes comprising pumping ultrapure water at a selected flow rate through a transfer pipe to a nozzle with one jet opening or a plurality of jet openings inside a hollow cylinder; using the one jet opening or the plurality of jet openings in the nozzle to jet the blended composition into the hollow cylinder; wherein the selected flow rate creates a vortex of the blended composition inside the hollow cylinder that encapsulates the solutes and reduce the size of the water clusters in the blended composition.

In some embodiments, the disclosure provides processes and apparatus for encapsulating one or more solutes in a water cluster comprising pumping a solution of ultrapure water through a transfer pipe and a nozzle to a hollow cylinder at a selected flow rate. In embodiments, the nozzle is located at the proximal end of the hollow cylinder and comprises an intake hole in a proximal face of the nozzle connected to the transfer pipe and one or more jet openings in a distal face of the nozzle that are in contact with a chamber defined by the hollow cylinder. In some embodiments, the width of the chamber is between about 2 to about 6 inches, the length of the chamber is between about 15 to about 20 inches, and the selected flow rate of ultrapure water in the transfer pipe and chamber is between about 10 to about 25 gallons per minute.

In some embodiments, the flow rate of ultrapure water in the transfer pipe is about 10 to about 25 gallons per minute. In particular embodiments, the flow rate of ultrapure water in the transfer pipe is about 10, about 11, about 12, about 13, about 14, about 15, about 16, about 18, about 20, about 22, about 24, or about 25 gallons per minute. In certain embodiments, the flow rate in a 1" diameter transfer pipe is between about 12 to about 18 gal/min. In certain embodiments, the flow rate in a 1" diameter transfer pipe is between about 14 to about 16 gallons per minute.

In other embodiments, the flow rate of ultrapure water in the transfer pipe results in a flow volume per minute which is a multiple of the hollow cylinder volume, the multiple selected from the group consisting of about 12 to about 13, about 13 to about 14, about 14 to about 15, about 15 to about 16, about 16 to about 17, about 17 to about 18, about 18 to about 19, and a combination thereof.

In embodiments of the disclosure, when the ultrapure water passes through the jet openings at the selected flow rate, creating a vortex of ultrapure water in contact in an inner surface of the chamber, a second solution is generated. The second solution produced after passing through the transfer pipe, nozzle, and hollow cylinder thus comprises a solute encapsulated within water clusters that have a median size of between about 2 to about 400 nanometers. In some embodiments, the second solution containing the solute encapsulated in water clusters is collected as it exits the cylinder.

In some embodiments, the present disclosure provides a process for reducing water cluster sizes in a composition comprising or consisting essentially of ultrapure water and a solute, the process comprising: choosing an amount of a solute to add to a volume of ultrapure water; adding the amount of the solute to the volume of ultrapure water in a mixing tank to form a blended composition containing the solute in the ultrapure water; pumping the blended composition at a selected flow rate from the mixing tank to a nozzle with one jet opening or a plurality of jet openings inside a hollow cylinder; using the one jet opening or the plurality of jet openings in the nozzle to jet the blended composition at a higher flow rate into the hollow cylinder; using the higher flow rate of the blended composition from the one jet opening or the plurality ofj et openings inside the hollow cylinder to reduce sizes of the water clusters in the blended composition of the solute in the ultrapure water; removing the composition with the reduced size water clusters containing the solute at the selected flow rate from inside the hollow cylinder; and using the reduced size water clusters containing the solute in the medium to improve the bioavailability of the solute.

In some embodiments, the present disclosure provides a process for reducing water cluster sizes in a composition comprising or consisting essentially of ultrapure water and a solute, wherein the solute comprises a ionizable salt, and wherein the amount of the ionizable salt added per gallon of the ultrapure water may be selected from the group consisting of between about 10 micrograms to about 50 micrograms, about 50 micrograms to about 100 micrograms, about 100 micrograms to about 200 micrograms, about 200 micrograms to about 400 micrograms, about 400 micrograms to about 800 micrograms, about 800 micrograms to about 1.6 milligrams, about 1.6 milligrams to about 3.2 milligrams, about 3.2 milligrams to about 6.4 milligrams, about 6.4 milligrams to about 30 milligrams, and a combination thereof.

In some embodiments, the present disclosure provides a process for reducing water cluster sizes in a composition comprising or consisting essentially of ultrapure water and a solute, wherein the selected flow rate from the mixing tank to the nozzle may result in a flow volume per minute which is a multiple of the hollow cylinder volume, the multiple selected from the group consisting of about 1 to 2, about 2 to 3, about 3 to 4, about 4 to 5, about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24 to 25, about 25 to 26, about 26 to 27, about 27 to 28, about 28 to 29, or about 29 to 30.

In some embodiments, the present disclosure provides a process for reducing water cluster sizes in a composition comprising or consisting essentially of ultrapure water and a solute, wherein the hollow cylinder has an inner width in inches which may be selected from the group consisting of between about 1 to 2 inches, about 2 to 3 inches, about 3 to 4 inches, about 4 to 5 inches, about 5 to 6 inches, about 6 to 7 inches, about 7 to 8 inches, about 8 to 9 inches, about 9 to 10 inches, about 10 to 11 inches, about 11 to 12 inches, about 12 to 13 inches, about 13 to 14 inches, about 14 to 15 inches, about 15 to 16 inches, about 16 to 17 inches, about 17 to 18 inches, about 18 to 19 inches, about 19 to 20 inches, and a combination thereof.

In some embodiments, the present disclosure provides a process for reducing water cluster sizes in a composition comprising or consisting essentially of ultrapure water and a solute, wherein the hollow cylinder has an inner length in inches that may be selected from the group consisting of between about 2 to 4 inches, about 4 to 6 inches, about 6 to 8 inches, about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, about 26 to 28 inches, about 28 to 30 inches, about 32 to 34 inches, about 34 to 36 inches, about 36 to 38 inches, about 38 to 40 inches, about 40 to 42 inches, about 42 to 44 inches, about 44 to 46 inches, about 46 to 48 inches, about 48 to 50, about 50 to 52, about 52 to 54, about 54 to 56, about 56 to 58, about 58 to 60, about 60 to 62, about 62 to 64, about 64 to 66, about 66 to 68, about 68 to 70, about 70 to 72, about 72 to 74, about 74 to 76, about 76 to 78, about 78 to 80 and a combination thereof.

In some embodiments, the present disclosure provides a process for reducing water cluster sizes in a composition comprising or consisting essentially of ultrapure water and a solute, wherein the ratio of the nozzle outer diameter in inches to the hollow cylinder inner diameter in inches is a ratio which may be selected from the group consisting of about a ratio of 1:1.15 to about 1:1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.30 to about 1:4.60, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of about 1:6.50 to about 1:7.50, and about a ratio of 1:7.50 to about 1:12.0, and a combination thereof.

In some embodiments, the present disclosure provides a process for reducing water cluster sizes in a composition comprising or consisting essentially of ultrapure water and a solute, wherein nozzle may have the one jet opening or the plurality of the jet openings selected from the group consisting of 1, 2, 3, 4, 5, 6, 7, 8, 9, 10, 11, 12, 13, 14, 15, 16, 17, 18, 19, and 20.

In some embodiments, the present disclosure provides a process for reducing water cluster sizes in a composition comprising or consisting essentially of ultrapure water and a solute, wherein the ratio of sum total area of jet openings on a nozzle outer side to area of nozzle inner diameter may be selected from the group consisting of the ratio of about 0.01 to 0.05, a ratio of about 0.05 to 0.10, a ratio of about 0.10 to 0.15, a ratio of about 0.15 to 0.20, a ratio of about 0.20 to 0.25, a ratio of about 0.25 to 0.30, a ratio of about 0.30 to 0.35, a ratio of about 0.35 to 0.40, a ratio of about 0.40 to 0.45, a ratio of about 0.45 to 0.50, a ratio of about 0.50 to 0.55, a ratio of about 0.55 to 0.60, a ratio of about 0.60 to 0.65, a ratio of about 0.65 to 0.70, a ratio of about 0.70 to 0.75, a ratio of about 0.75 to 0.80, a ratio of about 0.80 to 0.85, a ratio of about 0.85 to 0.90, a ratio of about 0.90-1.0, a ratio of about 1.0 to 1.2, a ratio of about 1.2 to 1.5, a ratio of about 1.5 to 1.7, and a combination thereof.

In some embodiments, the present disclosure provides a process for reducing water cluster sizes in a composition comprising or consisting essentially of ultrapure water and a solute, wherein the nozzle may have one curved bore hole jet opening or a plurality of the curved bore hole jet openings providing an average redirection of the jet opening angle in degrees which may be selected from the group consisting of 0, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90 degrees. In some embodiments, the nozzle has the curved bore hole jet opening providing the redirection of the jet opening angle as a clockwise redirection of the jet opening angle or as a counterclockwise redirection of the jet opening angle.

In some embodiments, the present disclosure provides a process for reducing water cluster sizes in a composition comprising or consisting essentially of ultrapure water and a solute, wherein the hollow cylinder has an inner width in inches, which may be selected from the group consisting of between about 3 to 4 inches, about 4 to 5 inches, about 5 to 6 inches, about 6 to 7 inches, about 7 to 8 inches, and a combination thereof, and wherein the hollow cylinder has an inner length in inches selected from the group consisting of between about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, and a combination thereof.

In some embodiments, the present disclosure provides a process for reducing water cluster sizes in a composition comprising or consisting essentially of ultrapure water and a solute, wherein the selected flow rate from the mixing tank to the nozzle results in a flow volume per minute which is a multiple of the hollow cylinder volume, the multiple selected from the group consisting of about 12 to 13, about 13 to 14, about 14 to 15, about 15 to 16, about 16 to 17, about 17 to 18, about 18 to 19, and a combination thereof. In some embodiments, the reduced size water clusters containing the solute in the aqueous medium have a median water cluster size from about 3 nanometers to about 300 nanometers.

Embodiments of the disclosure provide an apparatus for producing reduced sized water clusters comprising a hollow cylinder comprising an enclosed cylinder top, an enclosed cylinder bottom, and an inner surface defining a hollow chamber; a nozzle situated at the center of the cylinder top comprising a proximal portion and a distal portion; the nozzle further comprising an intake hole in the proximal portion of the nozzle connected to a transfer pipe directing flow into the nozzle; and one or more curved bore hole jet openings in the distal portion of the nozzle in contact with the hollow chamber. In some embodiments, the curved bore hole jet openings are oriented at an angle between 0 degrees and 90 degrees relative to a longitudinal axis of the hollow cylinder.

In certain embodiments, the inner width of the hollow cylinder is between about 3 to 4 inches, about 4 to 5 inches, about 5 to 6 inches, about 6 to 7 inches, or about 7 to 8 inches. In certain embodiments, the inner length of the hollow cylinder is between about 8 to 10 inches, about 10 to 12 inches, about 12 to 14 inches, about 14 to 16 inches, about 16 to 18 inches, about 18 to 20 inches, about 20 to 22 inches, about 22 to 24 inches, or about 24 to 26 inches.

This disclosure is further illustrated by the following examples, which are provided to facilitate the practice of the disclosed methods. These examples do not limit the scope of the disclosure in any way.

EXAMPLES

Example 1: Preparation of Water Clusters According to the Disclosure

Figure 3A:
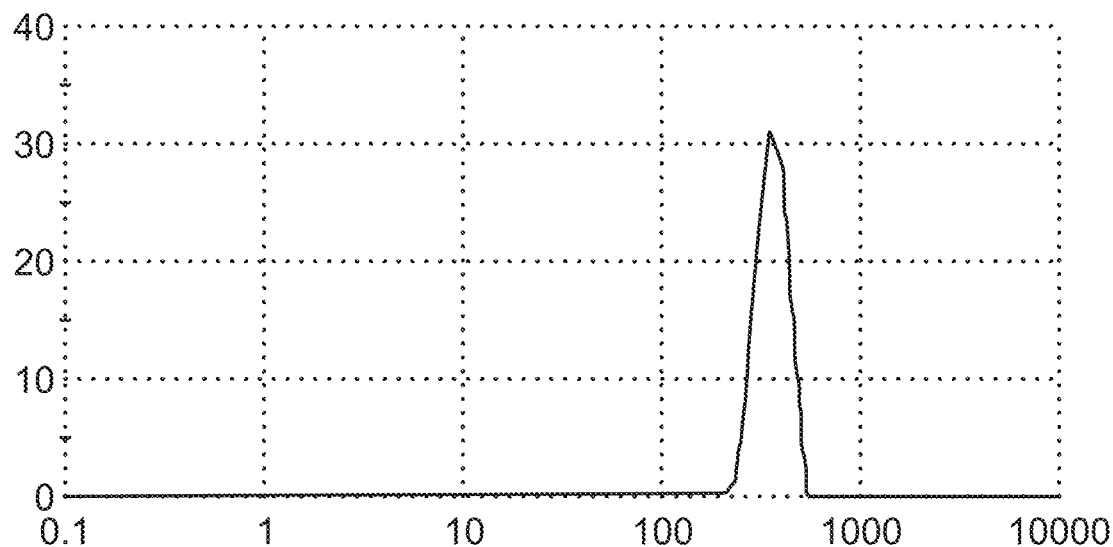
Figure 3B:
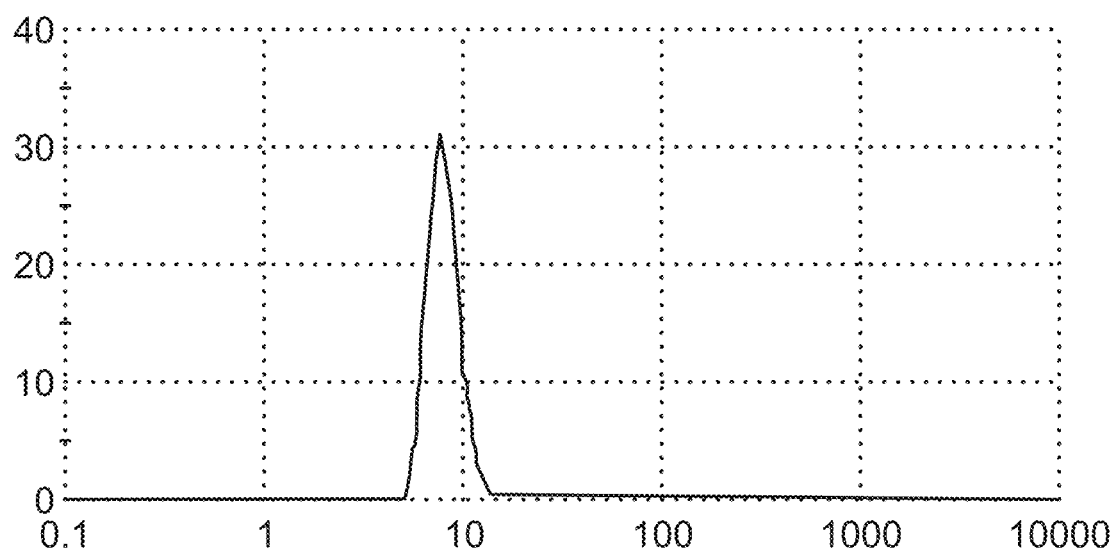

As demonstrated in FIG. 3, water clusters prepared according to the disclosure reduce sizes of water clusters in blended aqueous compositions comprising ultrapure water and encapsulated solutes. The Malvern Zetasizer was used to measure the median sizes of water cluster diameter before and after ultrapure water was prepared according to embodiments of the disclosure. Zetasizer measurements of water cluster sizes in a first sample taken before the solution entered the nozzle and hollow cylinder has a median water cluster diameter of 358 nanometers. A sample taken after exiting the hollow cylinder has a median water cluster size of 8 nanometers.

A second sample measured before the solution entered the nozzle and hollow cylinder has a median water cluster size of 286 nanometers (nm). A second sample taken after exiting the hollow cylinder has a median water cluster sizes of 2.5 nanometers.

A control sample was processed at a non-optimal flow rate. The median size of water clusters taken before and after passing through the hollow cylinder have a median water cluster size of 293 and 310 nm, respectively, demonstrating that the surprising and unexpected water cluster compositions disclosed herein are attributable to the methods and apparatus of the disclosure.

Example 2: Storage Stability

A sample composition prepared according to the disclosure was stored for 2 years and the cluster sizes measured by Zetasizer remained substantially unchanged over time.

Example 3: Hydration Study

A hydration experiment was performed to confirm the improved bioavailability and hydration properties of embodiments of the present invention compared to existing sports drinks or other hydration drinks used by football players.

30 subjects were administered a hydration formulation of the present invention. An additional group of 20 subjects was administered a water formulation embodiment of the present invention comprising Powerade™ sports drink powder encapsulated in water clusters in ultrapure water according to the disclosure. A control group was administered a conventional hydration formulation. All subjects self-administered the hydration formulations as needed.

All subjects were collegiate football players and were observed during strenuous exercise over the course of a college football season.

In warm to very hot weather, control subjects experienced 22 dehydration emergencies requiring intravenous fluid treatment. In contrast, subjects administered hydration formulations according to the disclosure experience no hydration emergencies requiring intravenous fluid.

Even in cool weather, control subjects experienced 7 dehydration emergencies requiring intravenous fluid treatment. In contrast, subjects administered a hydration formulation according to the disclosure experienced no hydration emergencies requiring intravenous fluid.

Overall, control subjects experienced 32 dehydration emergencies requiring intravenous fluid treatment. In contrast, subjects administered a hydration formulation according to the disclosure experienced no hydration emergencies requiring intravenous fluid.

Example 4: Double-Blind Hydration Study

A further double-blind placebo controlled study measures water clusters in ultrapure water of the disclosure versus controls to determine the influence on sports performance, mental acuity and hydration when subjected to high levels of physical stress.

Structure of Study: 15 participants are selected and broken into 6 total sessions: 3 sessions administering hydrosome water and 3 sessions with standard water. The study is double blinded. 2 days were allotted between each session to allow for recovery time. Water was administered at the same time every day and the same workout regimen was conducted in each session.

Testing protocol. Subjects are tested the same time of day every day during the course of the study. Subjects use a recumbent bicycle to perform the same physical regimen each session. Subjects are provided 5 minutes to stretch prior to exercise. Subjects are then required to maintain a specific number of revolutions per minute (RPM) at a specified resistance level for 10 minutes on the recumbent bike. Subjects are given a 3-minute break before beginning a max out session. For the last 3 minutes subjects will be asked to max out—that is push their physical threshold and see the overall distance that can be covered in those 3 minutes. Subjects are given a mental acuity test consisting of basic math problems promptly after completing the max out session.

Measurements:

The following parameters are measured prior to the session: total body water; intra-cellular water; extra-cellular water; phase angle; body weight; and heart rate.

The following parameters are measured during the session: heart rate; total distance covered on the recumbent bike.

The following parameters are measured after the session: mental acuity test, measuring time to completion and correct response rate; recovering heart rate over 20 minutes; total body water; intra-cellular water; extra-cellular water; total composition of their extra-cellular water; and phase angle.

Testing Equipment:

RJL—Quantum 4—Body Composition Analyzer: this measures intra-cellular, extra-cellular water and phase angle.

A simple scale for measuring the subject weight.

Garmin heart rate monitor: a Garmin monitor that can measure heart rate and automatically store it to a computer.

Example 5: Human Cell Absorption Study

Propidium iodide solutions were prepared according to embodiments of the disclosure or using conventional water means. The solutions were applied to human cells and incubated for the times presented in FIG. 4. After incubations, staining of DNA by propidium iodide was visualized using UV microscopy.

Figure 4:
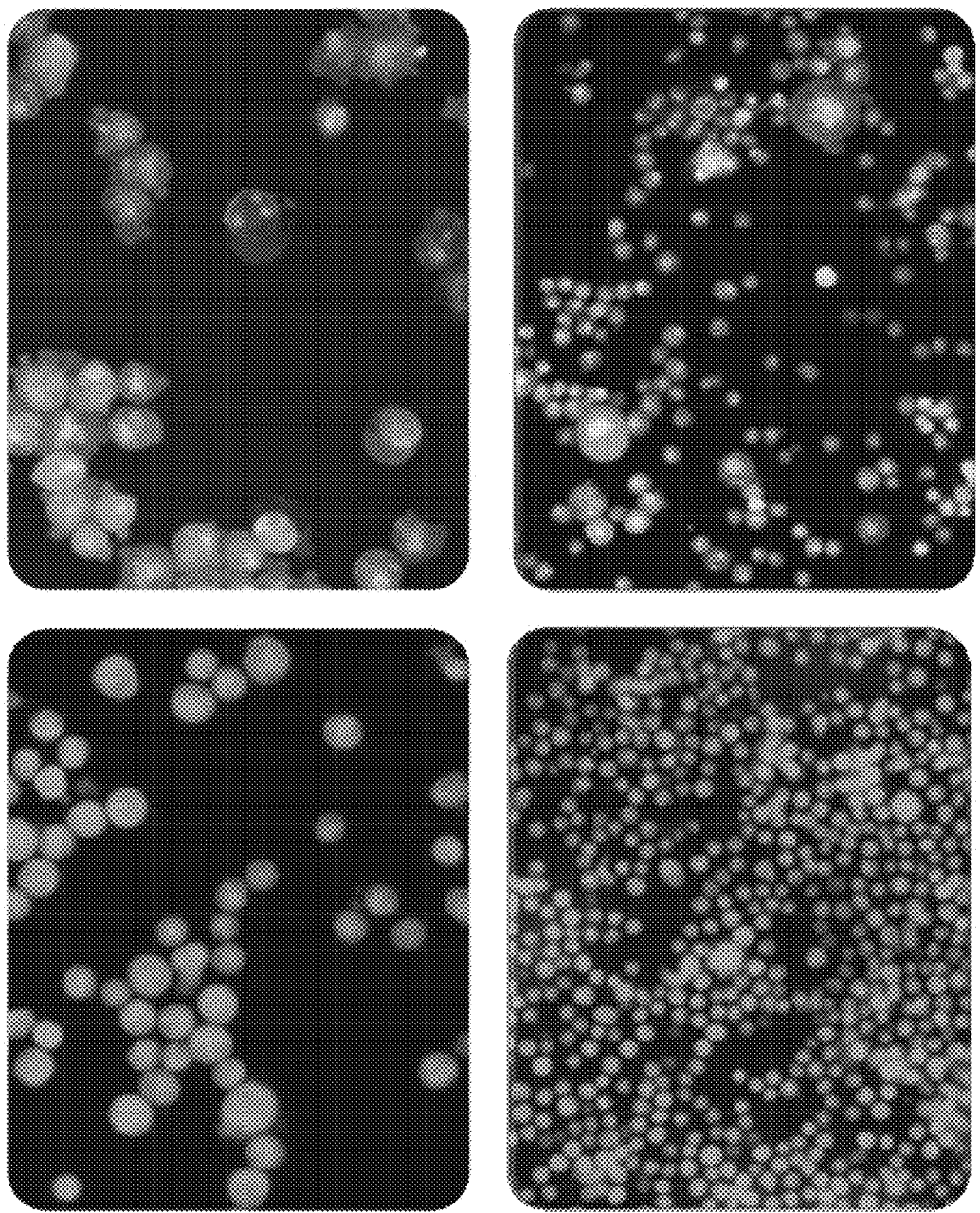

FIG. 4 demonstrates that propidium iodide encapsulated by the water cluster of the present disclosure is able to access the interior of cell nuclei at 10 and 30 minutes ("NanoPI," top and bottom right, respectively), whereas propidium iodide in control water is not able to enter cells ("Macro PI Control" at left).

Example 6: Chicken Feed Study

Pen mates were fed medicated feed prepared in normal water, or water comprising 1% or 2% water clusters in ultrapure water according to the disclosure. A fourth pen was fed non-medicated feed prepared in water comprising 2% water clusters in ultrapure water according to the disclosure. Medicated feed comprises the industry standard combination of antibiotics and hormones necessary to maintain poultry viability under conventional, non-free range living conditions. Fertilizer was encapsulated in water clusters according to the methods of the disclosure, and the resulting solution was diluted in ultrapure water to arrive at the indicated at a ratio of 1:100 (1% water clusters, or hydrosomes) or 1:50 (2% water clusters, or hydrosomes).

Pen mates fed water comprising 1% or 2% water clusters in ultrapure water according to the disclosure grew faster and experienced lower mortality rates than those fed medicated feed in conventional water. Even non-medicated feed showed better outcomes in water clusters in ultrapure water according to the disclosure than medicated feed prepared in conventional water. See Table 2 below for detailed results.

TABLE 2

Chicken Feed Study

| Pen | Treatment | Per Bird Weight | Avg. Daily Gain | Feed Efficiency | Death Loss | Condemns |
| --- | --- | --- | --- | --- | --- | --- |
| 1 | No Hydrosome Medicated Feed | 5.94 | .1320 | 1.814 | 15% | 2 |
| 2 | 1% Hydrosome Medicated Feed | 6.71 | .1491 | 1.769 | 10% | 0 |
| 3 | 2% Hydrosome Medicated Feed | 6.4 | .1427 | 1.857 | 5% | |
| 4 | 2% Hydrosome Non-Medicated Feed | 6.52 | .1447 | 1.748 | 5% | 0 |

Example 7: Sod Farm Study

Fertilizer solutions were prepared by blending 100 mL of fertilizer into conventional water, or blending 0.2 mL fertilizer into water prepared according to the disclosure and encapsulated in water clusters according to the disclosure.

Figure 5:
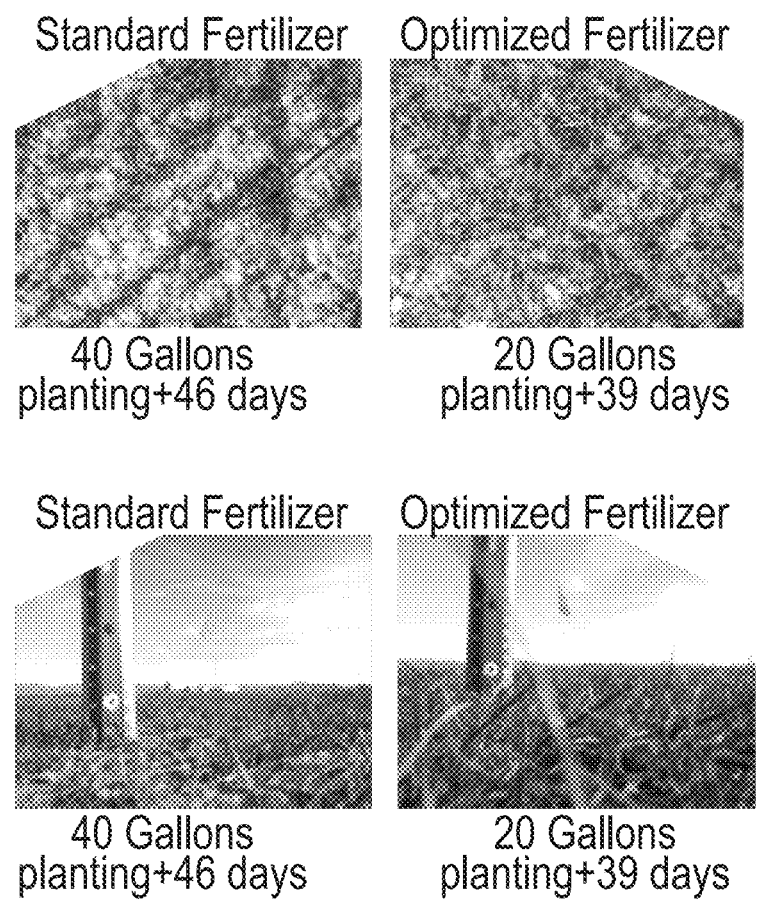

Sod was watered with 40 gallons of water per day with dissolved fertilizer prepared conventionally or 20 gallons of water per day prepared with water cluster encapsulated fertilizer according to embodiments of the disclosure. See FIG. 5 and Table 3 (Note the water cluster, or hydrosome, is referred to as a "Hydrozome" in FIG. 5). Sod exposed to fertilizer water prepared according to the disclosure had better outcomes than sod exposed to twice the amount of conventionally prepared fertilizer solutions.

Sod watered with water cluster encapsulated fertilizer according to embodiments of the disclosure had 19.1% higher grass tissue moisture.

Sod watered with water cluster encapsulated fertilizer according to embodiments of the disclosure was harvested 25% sooner; the grass was fully grown and ready for harvest 25% sooner than control group.

Soil watered with water cluster encapsulated fertilizer according to embodiments of the disclosure showed 112% Higher Soil Moisture Content. (Table 3.)

TABLE 3

Tissue Moisture Content Test Results

| | Sample of Grass Tissue | | |
|---|---|---|---|
| | 40 gal Standard Fertilizer | 20 gal Hydrosome Fertilizer | % Difference |
| Tissue Moisture (%) | 49.25 | 59.1 | 20.1 |
| Sodium Content in ppm | 769.966 | 1505.804 | 95.56 |
| Millimohs per centimeter | 1.20 | 2.35 | |

Sod watered with water cluster encapsulated fertilizer according to embodiments of the disclosure had higher content of core nutrients even though it was watered with less fertilizer. (Table 4.)

TABLE 4

Soil Moisture Content Test Results

| | Soil Core Sample | | |
|---|---|---|---|
| | 40 gal Standard Fertilizer | 20 gal Hydrosome Fertilizer | % Difference |
| Soil Moisture (%) | 9.0 | 99.1 | 112.22 |

Sod watered with water cluster encapsulated fertilizer according to embodiments of the disclosure showed much higher seed germination rate. (Table 5.)

TABLE 5

Macro Nutrient Test Results

| | Sample of Grass Tissue | | |
|---|---|---|---|
| | 40 gal Standard Fertilizer | 20 gal Hydrosome Fertilizer | % Difference |
| Nitrogen, % N | 3.84% | 3.96% | 3.12% |
| Phosphorous, % P | 0.28% | 0.32% | 14.28% |
| Potassium, % K | 2.55% | 2.74% | 7.45% |
| Protein Content | 24 | 24.75 | 3.12% |

Example 7: 3-Day Alfalfa Sprouting Study

Figure 6:
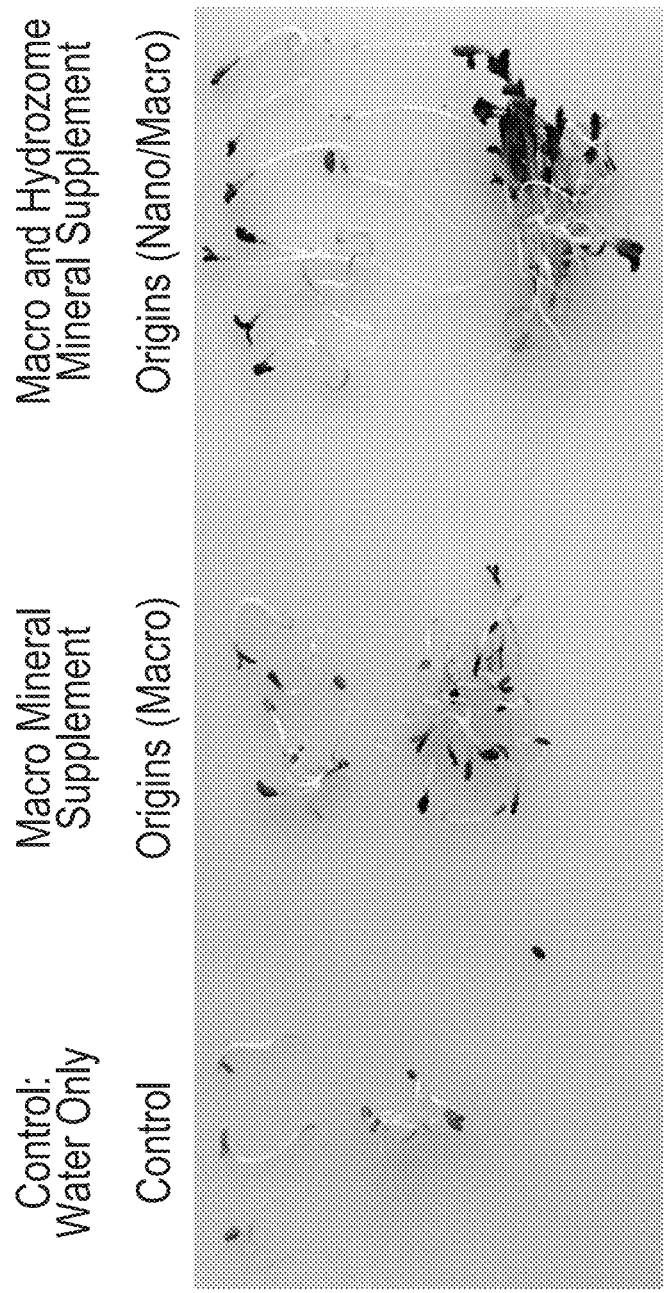

Sprouting alfalfa plants were exposed to control water, macromineral supplement, and macromineral supplement encapsulated in water clusters according to embodiments of the disclosure. See FIG. 6. Plants exposed to macromineral supplement encapsulated in water clusters according to embodiments of the disclosure experienced greater growth rates and improved overall outcomes.

Example 8: 15-Day Pea Sprouting and Heat Tolerance Study

Figure 7:
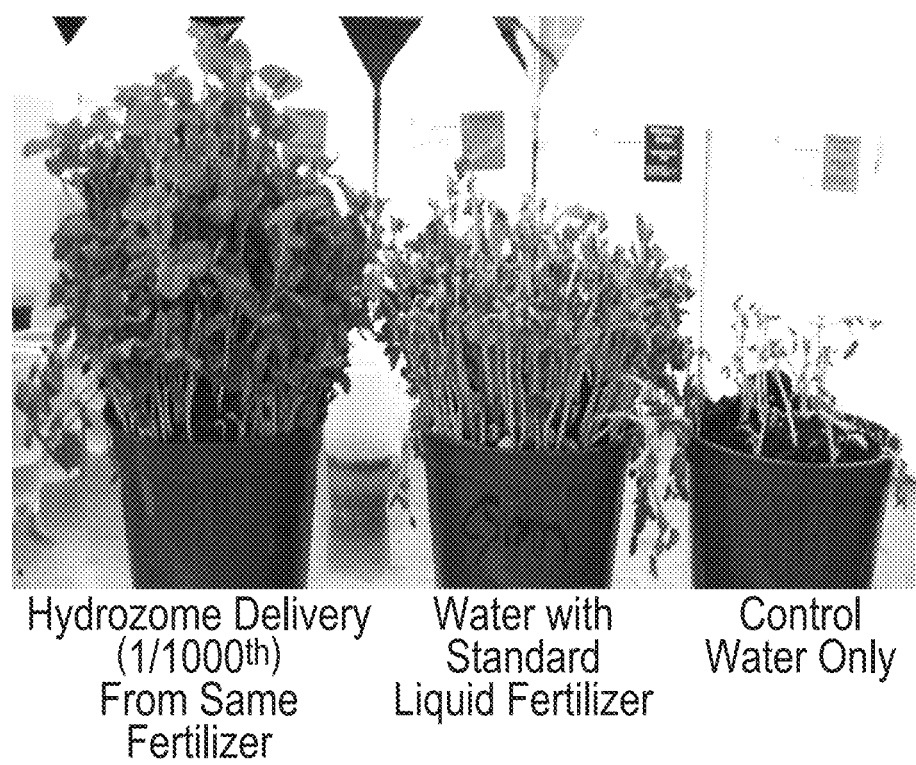
Figure 8:

Sprouting pea plants were exposed to control water, water with dissolved fertilizer prepared conventionally, and water prepared with fertilizer encapsulated in water clusters according to embodiments of the disclosure. See FIG. 7. Seeds were planted and watered for 13 days. No water was given during the last two days and the plants were left outside in 95 degree heat to test their heat tolerance. The hydrosome plants were healthier, grew more quickly, and because of extensive root structure, were much more heat/drought tolerant that comparative pots. Thus, plants exposed to fertilizer encapsulated in water clusters according to embodiments of the disclosure experienced greater growth rates and improved overall outcomes.

Example 9: Safflower Drought Resistance

Safflower plants grown in adjacent fields during heat and drought conditions in Northern Utah. Safflower plants were watered with dissolved fertilizer prepared conventionally and water prepared with fertilizer encapsulated in water clusters according to embodiments of the disclosure. Fields were watered with the same amount of fertilizer. FIG. 10 shows that safflower plants watered with fertilizer encapsulated in water clusters according to embodiments of the disclosure (hydrosome) showed improved drought tolerance, improved overall health of the plant, improved root structure, lower branching, and increased flowering.

Example 10: Oxidative Reduction Potential

Water clusters comprising ultrapure water according to the disclosure (hydrosome water) exhibits an extremely high negative redox potential. Sample measurements were obtained from the presently disclosed water compositions in comparison with reference products. The oxidative reduction potential of each water sample was measured with an Oakton water testing meter.

| Brand: | pH: | ORP (mV) | RH2 |
|---|---|---|---|
| Hydrosome water | 8.2 | −94 | 19.9333333 |
| Essentia | 8.57 | 58 | 25.74 |
| Smart Water | 7.2 | 378 | 33.6666667 |
| Fiji Water | 6.65 | 406 | 33.5 |
| Dannon | 7.84 | 546 | 40.5466667 |
| Dasani | 7.2 | 378 | 33.6666667 |
| Penta | 6.7 | 789 | 46.3666667 |
| Evian | 7.53 | 390 | 34.7266667 |
| Zephyrhills | 7.57 | 362 | 33.8733333 |
| Deja Blue | 6.28 | 644 | 40.6933333 |

The ORP readings indicate the water's ability to act as a potent antioxidant or reducing agent within the body. The ORP measures the capacity of a solution to either release or accept electrons from chemical reactions. The ORP value, much like pH, is important for determining water quality.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims.

The invention claimed is:

1. A composition comprising ultrapure water and a solute, wherein the composition is prepared by a process consisting essentially of:
   a) pumping the ultrapure water and the solute through a transfer pipe and a nozzle into a hollow cylinder, wherein the nozzle is located at the proximal end of the hollow cylinder and comprises:

(i) an intake hole in a proximal face of the nozzle connected to the transfer pipe; and (ii) one or more jet openings in a distal face of the nozzle that open into a chamber defined by the hollow cylinder, wherein the ultrapure water passing through the one or more jet openings creates a vortex of ultrapure water in contact with an inner surface of the chamber; and b) obtaining the composition from the chamber, wherein the ultrapure water of the composition prepared by the process increases cell permeability of the solute as compared to ultrapure water of a composition not prepared by the process.

\* \* \* \* \*